US011717555B2

(12) United States Patent
Li et al.

(10) Patent No.: US 11,717,555 B2
(45) Date of Patent: Aug. 8, 2023

(54) PHARMACEUTICAL COMPOSITIONS HAVING A SELECTED RELEASE DURATION

(71) Applicant: Foresee Pharmaceuticals Co., Ltd., Taipei (TW)

(72) Inventors: Yuhua Li, Landenberg, PA (US); Andrew Guarino, Newark, DE (US)

(73) Assignee: Foresee Pharmaceuticals Co., Ltd., Taipei (TW)

( * ) Notice: Subject to any disclaimer, the term of this patent is extended or adjusted under 35 U.S.C. 154(b) by 379 days.

(21) Appl. No.: 16/954,984

(22) PCT Filed: Dec. 18, 2017

(86) PCT No.: PCT/US2017/066968
§ 371 (c)(1),
(2) Date: Jun. 17, 2020

(87) PCT Pub. No.: WO2019/125358
PCT Pub. Date: Jun. 27, 2019

(65) Prior Publication Data
US 2020/0390849 A1      Dec. 17, 2020

(51) Int. Cl.
*A61K 38/09* (2006.01)
*A61K 47/34* (2017.01)
*A61K 9/00* (2006.01)
*A61K 47/22* (2006.01)

(52) U.S. Cl.
CPC ............ *A61K 38/09* (2013.01); *A61K 9/0024* (2013.01); *A61K 47/22* (2013.01); *A61K 47/34* (2013.01)

(58) Field of Classification Search
CPC ...... A61K 38/09; A61K 9/0024; A61K 47/22; A61K 47/34
See application file for complete search history.

(56) References Cited

U.S. PATENT DOCUMENTS

| | | |
|---|---|---|
| 4,938,763 A | 7/1990 | Dunn et al. |
| 5,278,201 A | 1/1994 | Dunn et al. |
| 5,278,202 A | 1/1994 | Dunn et al. |
| 5,324,519 A | 6/1994 | Dunn |
| 5,340,849 A | 8/1994 | Norton et al. |
| 5,487,897 A | 1/1996 | Polson |
| 5,599,552 A | 2/1997 | Norton et al. |
| 5,681,873 A | 10/1997 | Norton et al. |
| 5,702,716 A | 12/1997 | Dunn |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,759,563 A | 6/1998 | Yewey et al. |
| 5,780,044 A | 7/1998 | Yewey et al. |
| 5,792,469 A | 8/1998 | Tipton et al. |
| 5,945,115 A | 8/1999 | Dunn et al. |
| 5,990,194 A | 11/1999 | Dunn et al. |
| 6,143,314 A | 11/2000 | Chandrashekar |
| 6,261,583 B1 | 6/2001 | Dunn et al. |
| 6,355,657 B1 | 3/2002 | Osborne |
| 6,395,293 B2 | 5/2002 | Polson |
| 6,461,631 B1 | 10/2002 | Dunn et al. |
| RE37,950 E | 12/2002 | Dunn et al. |
| 6,528,080 B2 | 3/2003 | Dunn et al. |
| 6,565,874 B1 | 5/2003 | Dunn et al. |
| 6,773,714 B2 | 8/2004 | Dunn et al. |
| 8,343,513 B2 | 1/2013 | Thanoo et al. |
| 2004/0010224 A1 | 1/2004 | Bodmeier |
| 2016/0106804 A1 | 4/2016 | Li et al. |
| 2016/0331802 A1 | 11/2016 | Li et al. |

FOREIGN PATENT DOCUMENTS

| | | |
|---|---|---|
| CN | 101400363 A | 4/2009 |
| CN | 107075541 A | 8/2017 |
| JP | 2002528403 A | 9/2002 |
| JP | 2004510807 A | 4/2004 |
| JP | 2009523798 A | 6/2009 |
| JP | 2017531697 A | 10/2017 |

(Continued)

OTHER PUBLICATIONS

Bishop, "Weak acid equilibrium," Chiral publishing company, accessed Feb. 20, 2023 at URL preparatorychemistry.com/Bishop_weak_acid_Equilibrium.htm, (2013) (Year: 2013).*
Japanese Application No. 2020-552664, Japanese Office Action dated Jul. 5, 2022, 11 pages.
Korean Application No. 10-2020-7020359, Korean Office Action dated Jun. 24, 2022, 14 pages.
Saudi Arabian Application No. 520412229, Saudi Arabian Substantive Examination Report dated Mar. 30, 2022, 7 pages.
European Application No. 17935525, Supplementary European Search Report dated Jun. 22, 2021, 4 pages.
Korean Application No. 10-2020-7020359, Notice of Final Rejection dated Nov. 8, 2022, 11 pages.
The International Search Report and the Written Opinion dated Mar. 7, 2018 for related PCT/US 2017/066968.
International Preliminary Report on Patentability dated Jun. 23, 2020 for related PCT/US 2017/066968.
Government of Canada, "Health Product InfoWatch"—Jan. 2017, retrieved from: https://www.canada.ca/en/health-canada/services/drugs-health-products/medeffect-canada/health-product-infowatch/health-product-infowatch-january-2017-1.html#mae on Apr. 15, 2021.

(Continued)

*Primary Examiner* — Julie Ha
*Assistant Examiner* — Kristina M Hellman
(74) *Attorney, Agent, or Firm* — MagStone Law, LLP; Enshan Hong

(57) ABSTRACT

The present invention provides for a stabilized biodegradable polymeric composition useful as a controlled release delivery system for peptide agents. The compositions of the present invention comprise a) a strong acid salt of a LHRH agonist or antagonist; b) a biodegradable polymer of poly (lactide-co-glycolide), wherein the ratio of lactide:glycolide of the copolymer is from 50:50 to about 100:0; and c) N-methyl-2-pyrrolidone (NMP), wherein the composition does not contain excess strong acid in addition to the strong acid used to form the salt of the LHRH agonist or antagonist. The composition, when injected, can provide a controlled release of leuprolide for a period of up to 6 months.

15 Claims, 8 Drawing Sheets

(56) References Cited

FOREIGN PATENT DOCUMENTS

| KR | 1020080089643 | 10/2008 |
| WO | 0024374 | 5/2000 |
| WO | 0230393 | 4/2002 |
| WO | 2007041410 A2 | 4/2007 |
| WO | 2007084460 A2 | 7/2007 |
| WO | 2011161531 A1 | 12/2011 |

OTHER PUBLICATIONS

Rossomando E. F. "(24] Ion-exchange chromatography", Methods in Enzymology, 1990, vol. 182, pp. 309-317.
Japanese Application No. 2020-552664,Japanese Office Action dated Nov. 22, 2021, 9 pages.
Singapore Application No. 11202004525T, Singapore Search Report and Written Opinion dated Jan. 24, 2022, 8 pages.
Office Action issued by Russian Patent Office dated Apr. 15, 2021 for related Russian Federation No. 2020117624.
Chinese Application No. 201780097703.2, First Chinese Office Action dated Apr. 13, 2023, 12 pages.
European Application No. 17935525.0, Extended European Examination Report dated Sep. 6, 2022, 6 pages.

* cited by examiner

Figure 1: *In vitro* release of leuprolide mesylate from different polymers compared with Eligard® 45 mg release Figure 2: Mean Serum Concentration-Time Profiles of Leuprolide in Male Rats after a Single Subcutaneous Administration Figure 3: *In vitro* release of LAMS and LAAc from PLA/NMP solution Figure 4: LAMS release from Eligard® 45mg polymer solution compared with Eligard® 45 mg release Figure 5: *In vitro* release of leuprolide mesylate from different PLGA polymers compared with release from PLA polymer

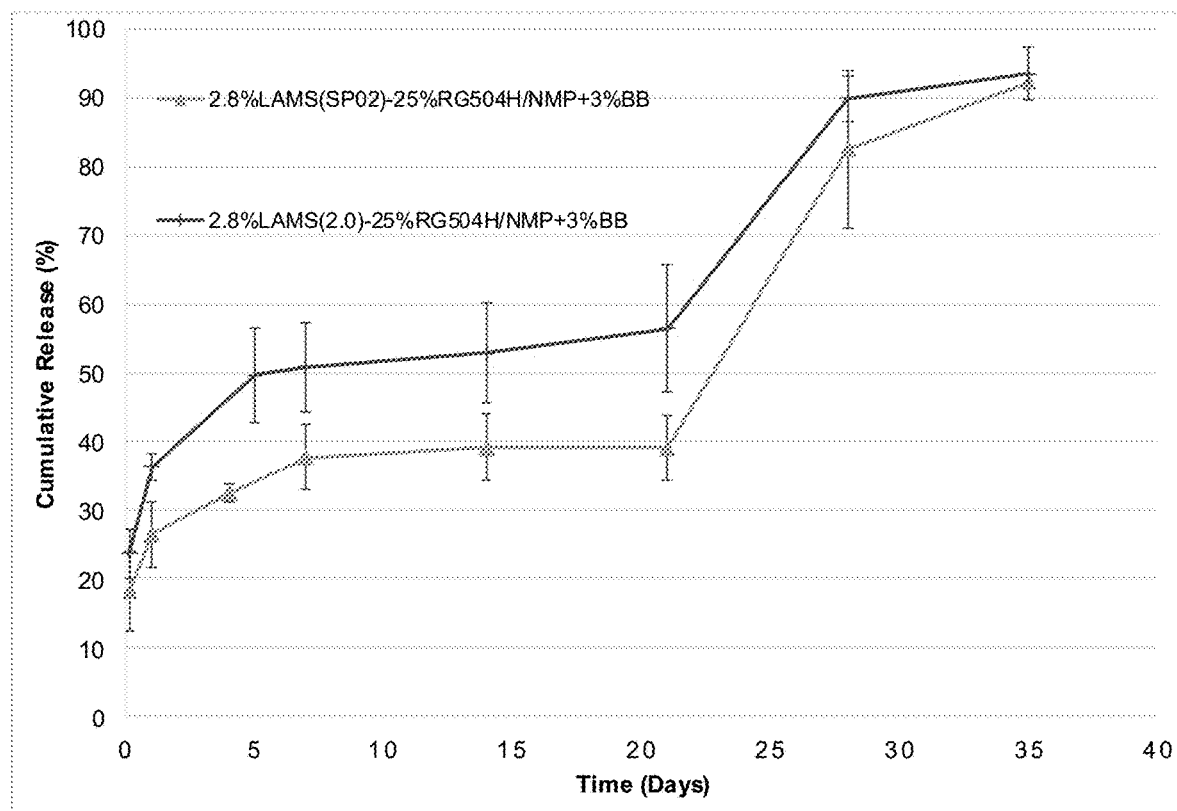
Figure 9: *In Vitro* Release of Leuprolide mesylate with a molar ratio of 1.6 and 2.0 from PLGA5050 Formulations in PBS at pH 7.4 at 37°C

US 11,717,555 B2

PHARMACEUTICAL COMPOSITIONS HAVING A SELECTED RELEASE DURATION

FIELD OF THE INVENTION

The field of the invention relates to a delivery system for the sustained and controlled release delivery of peptides with tailored delivery durations, and the process for making such a composition.

BACKGROUND OF THE INVENTION

Many peptide agents are not stable as they are easily hydrolyzed or degraded in vivo by enzymes resulting in a very short circulation half-life. Therefore, most of peptide medicines have been administered by injection, typically multiple times per day. Injection administration, however, is painful, very costly, and inconvenient. Often, the patient compliance is very challenging. For many peptide agents, particularly hormones, it requires the drug to be delivered continuously at a controlled rate over a long period of time, and thus a controlled release delivery system is desirable. Such systems may be provided by incorporating the peptides in biodegradable and biocompatible polymer matrices. Biocompatible and biodegradable polymers have been used as drug delivery carriers to provide sustained or delayed release of bioactive substances. The delivery systems are available in various injectable depot forms including liquid forms, suspensions, solid implants, microspheres, microcapsules and microparticles.

In one approach the polymer is dissolved in an organic solvent and then mixed with the peptide agents that is fabricated into the forms of microcapsules, microgranules or implantable rods by removing the organic solvent. The peptide agent is entrapped within the polymer matrices. Several products have been successfully developed by using biodegradable polymers in the forms of microparticles and solid rod implants, such as Lupron, Zoladex, Triptorelin, etc. Although these products appear to be effective, they have drawbacks and limitations, such as the large volume of suspending fluids for microparticles or surgical insertion of solid implants. These products are not very patient friendly. In addition, the manufacturing processes for producing sterile and reproducible products are complicated, resulting in high cost of manufacturing. It is highly desirable that a composition can be manufactured and used easily.

In one approach the polymer is dissolved in an organic solvent and then mixed with the peptide agents that is fabricated into the forms of microcapsules, microgranules or implantable rods by removing the organic solvent. The peptide agent is entrapped within the polymer matrices. Several products have been successfully developed by using biodegradable polymers in the forms of microparticles and solid rod implants, such as Lupron Depot®, Zoladex®, Triptorelin, etc. Although these products appear to be effective, they have drawbacks and limitations, such as the large volume of suspending fluids for microparticles or surgical insertion of solid implants. These products are not very patient friendly. In addition, the manufacturing processes for producing sterile and reproducible products are complicated, resulting in high cost of manufacturing. It is highly desirable that a composition can be manufactured and used easily.

Polyester is one of the most popular polymers used in biodegradable sustained drug delivery systems thus far. For example, poly(lactide-co-glycolide) or polylactide is the polymeric material used in Lupron Depot and Eligard® products for the treatment of advanced prostate cancer. These polyesters are biocompatible and degraded by typical biochemical pathways, such as hydrolysis and enzymolysis, to result in naturally occurring metabolic products. In order to maintain the product stability, Eligard requires the bioactive substance and carrier to be packaged separately and mixed immediately prior to injection. Reconstitution and route of administration errors have been reported with Eligard which could compromise the clinical efficacy of the product [*Canada Health Product Info Watch—January* 2017].

It is well recognized in the art that bioactive agent containing basic functional groups interacts with biodegradable polymer to catalyze (or expedite) the degradation of the polymer and form conjugate with the polymer and/or its degradation products. The interaction/reaction between the basic bioactive agents and polymer carriers may occur: 1) during formulation when the basic bioactive agents are incorporated in the polymer carrier, such as microencapsulation, injection molding, extrusion molding, mixing with polymer solutions in organic solvent, and the like; 2) during storage and 3) during the process of biodegradation and the release of bioactive agents in vivo.

U.S. Pat. No. 8,343,513 disclosed several ways to eliminate or reduce the reactions between bioactive agent containing nucleophilic functional groups and biodegradable polymer to generate impurities in the process to prepare microspheres. It describes that "the following general considerations should be kept in mind in any efforts to eliminate or reduce impurities in microspheres: (i) Higher the lactide content in PLGA microsphere, lower will be the amount of related substances and the microspheres prepared from 100% PLA will have least amount of related substances; (ii) higher the PLGA molecular weight, higher will be the related substances; higher the target load in PLGA, higher will be the level of the related substances; and (iii) lower the level of extractable oligomers in PLGA, higher will be the level of related substances; hydrophobic PLGA (end blocked PLGA) can produce more related substances compared to the hydrophilic PLGA (free acid end group)" [See U.S. Pat. No. 8,343,513, Column 11, second paragraph]. The overall teaching is to use low molecular weight polyesters having acid end groups with added significant additional amount of low pKa acid additives or oligomers. Examples of acid additives include lactic acid and glycolic acid which are monomer building blocks for the PLGA. The excess amount of acid additives has some limited success to reduce the generation of impurities within a short period of time (24 hours) in non-pharmaceutically acceptable solvents, such as dichloromethane and methanol. In addition, acidic additives cause low pH in the dispersed phase. It is well-known that low pH would cause tissue irritations. Thus, such dispersed phases may be used for manufacturing of microspheres, but are not suitable for administration to patients via direct injection.

Therefore, there is a need to develop a pharmaceutical composition that will minimize or prevent the interaction/reaction between the peptide agent and the polymer in an organic solution. There is a further need to develop a pharmaceutical composition that is stable with a satisfactory storage shelf life in a ready-to-use product configuration and can provide a controlled release of drug over a desired time.

SUMMARY OF THE INVENTION

It was previously discovered that injectable biodegradable polymeric compositions comprising peptide agents in the form of a salt formed with a strong acid (e.g., hydrochloric acid or methanesulfonic acid) exhibit much higher stability than those in the form of a salt formed with a weak acid (e.g., acetic acid) or in the form of the free base. Such beneficial salts of peptide agents may be formed through the neutralization of any basic groups of the peptide agents with a strong acid. When such beneficial salts of peptide agents formed with a strong acid were formulated into injectable biodegradable polymeric compositions, the interactions/reactions between the peptide agents and the polymer are minimized or prevented. Using such beneficial salts of peptide agents formed with a strong acid allows for the preparation of a stabilized injectable composition pre-filled in a single syringe in a ready-to-use configuration with satisfactory storage stability.

It was unexpectedly discovered that the polymers of such compositions degraded faster once injected in an aqueous environment than the polymers of compositions using a salt formed with a weak acid. This is surprising since the compositions comprising peptide agents in the form of a salt formed from a strong acid have a much higher storage stability and shelf-life, both in peptide purity and polymer molecular weight stability, than do the compositions formed using salts formed with weak acids. This finding can be used to formulate compositions of formulations with tailored release durations.

According to the product package insert, the commercially available product ELIGARD® is a sterile polymeric matrix formulation of leuprolide acetate for subcutaneous injection. It is designed to deliver leuprolide acetate at a controlled rate over a one-, three-, four or six-month therapeutic period.

ELIGARD® is prefilled and supplied in two separate, sterile syringes. One syringe contains the ATRIGEL® Delivery System and the other contains leuprolide acetate. ATRIGEL® is a polymeric (non-gelatin containing) delivery system consisting of a biodegradable poly (DL-lactide-co-glycolide) (PLGH or PLGA) polymer formulation dissolved in a biocompatible solvent, N-methyl-2-pyrrolidone (NMP).

The contents of two separate syringes are mixed immediately prior to administration. The two syringes are joined and the single dose product is mixed until it is homogenous. The mixture is not stable so it has to be used immediately or it has to be discarded if not used within 30 min. ELIGARD® is administered subcutaneously, where it forms a solid drug delivery depot.

PLGAH polymer is used for one-month product, while PLGA polymers are used in the three-, four- or six-month products. PLGH copolymer (with a molar ratio of DL-lactide to Glycolide=50:50) contains carboxyl end groups which expedite the degradation of the polymer. PLGA copolymer for 3 and 4-month products has a molar ratio of DL-lactide to Glycolide=75:25, while the PLGA copolymer for 6-month product has a molar ratio of DL-lactide to Glycolide=85:15. PLGA copolymers are manufactured with hexanediol as an initiator resulting in the PLGA copolymer with hydroxyl end groups at both ends.

The present inventors have found that by using a leuprolide salt formed with a strong acid in place of leuprolide acetate, the stability of the resulting formulation can be significantly improved. The stabilized final formulation can be prefilled in a single syringe with a suitable storage shelf-life.

However, although the formulation containing leuprolide mesylate or other strong acid salts is more stable during storage than that containing leuprolide acetate or other weak acid salts, it was surprisingly found that the PLGA polymers in the formulation containing leuprolide mesylate degraded faster than those in the formulation containing leuprolide acetate during in vitro and in vivo release. This property is quite counter intuitive and unexpected. This property can be advantageously used to tailor and fine tune the formulation to prepare better and improved products.

Accordingly, the present invention provides a stabilized injectable biodegradable polymeric composition for forming an economical, practical, and efficient controlled release delivery system for a LHRH agonist or antagonist. The present invention also provides a method of manufacturing and a method of use thereof. According to the present invention, the drug delivery system is produced easily and delivered conveniently to a subject such as a mammal or human. The compositions deliver a therapeutic amount of peptide over a desired, extended period of time, based on the specific composition of the biodegradable polymer used in the composition with the salt of a peptide formed from a strong acid. The compositions are both biocompatible and biodegradable, and disappear harmlessly after delivering the dose of the peptide agents.

The compositions in accordance with the present invention comprise a) a salt of a LHRH agonist or antagonist formed with a strong acid that minimizes or prevents the interaction/reaction between the peptide and the polymer in an organic solution; b) a biodegradable polymer; c) a pharmaceutically acceptable organic solvent, that when formulated together can deliver the LHRH agonist or antagonist over a 1-, 3-, 4- or 6-month period. According to the invention, the pharmaceutical composition may optionally include excipients to achieve optimal delivery of the peptide agent. The pharmaceutical composition may be a viscous or non-viscous liquid, gel or semisolid that moves as a fluid so that it may be injected using a syringe. The pharmaceutical composition may be pre-filled into one syringe to form a product in a ready-to-use configuration.

The compositions in accordance with the present invention comprise a) a mixture of a salt of a LHRH agonist or antagonist formed with a strong acid and a salt of a LHRH agonist or antagonist formed with a weak acid, wherein the molar ratio of strong acid to LHRH agonist or antagonist is from 1:1 to 2:1, wherein the composition does not contain excess acid in addition to the acids used to form the strong acid to LHRH agonist or antagonist; b) a biodegradable polymer; c) a pharmaceutically acceptable organic solvent, that when formulated together can deliver the LHRH agonist or antagonist over a 1-, 3-, 4- or 6-month period. According to the invention, the pharmaceutical composition may optionally include excipients to achieve optimal delivery of the peptide agent. The pharmaceutical composition may be a viscous or non-viscous liquid, gel or semisolid that moves as a fluid so that it may be injected using a syringe. The pharmaceutical composition may be pre-filled into one syringe to form a product in a ready-to-use configuration.

LHRH such as leuprolide, triptorelin, and goserelin contains two basic functional group, i.e., histidine and arginine which can form ion pairs with a suitable counter ion. A salt of a LHRH agonist or antagonist formed with a strong acid can achieve a stoichiometric normal ratio of strong acid to LHRH agonist or antagonist that equals to 2:1. The salt of a LHRH agonist or antagonist can also be prepared to contain a mixture of a strong acid and a weak acid, but the ratio of (strong acid+weak acid) to LHRH agonist or antagonist is less than or equal to 2:1. In the case of salt mixture, the molar ratio of strong acid to LHRH agonist or antagonist is from 1:1 to 2:1. By varying salt mixture composition or ratio, the release profile of an LHRH in an aqueous environment or human body can be tailored to achieve desired storage stability and drug delivery duration. The salt of a LHRH agonist or antagonist as disclosed herein has a pH (50 mg/mL in water) as determined by USP<791> method greater than 3, preferably greater than 4.

According to one embodiment of the present invention, the LHRH agonist or antagonist has either an N-terminal primary amine or side chain primary amine group covalently modified with hydrophilic and/or lipophilic moieties that may be produced through pegylation, acylation, and the like. Furthermore, both N-terminal primary amine and side chain primary amine groups of the peptide agents may also be covalently modified simultaneously with hydrophilic and/or lipophilic moieties through pegylation, acylation, and the like.

The strong acid may be any acid having a pKa in water less than 3, preferably less than 0. For example, a strong acid may be selected from, but not limited to, the group consisting of hydrochloric acid, hydrobromic acid, sulfuric acid, organic sulfuric acids, alkyl sulfuric acids of 1-40 carbons, nitric acid, chromic acid, methanesulfonic acid, trifluromethane sulfonic acid, organic sulfonic acids, trichloroacetic acid, dichloroacetic acid, bromoacetic acid, chloroacetic acid, cyanoacetic acid, 2-chloropropanoic acid, 2-oxobutanoic acid, 2-chlorobutanoic acid, 4-cyanobutanoic acid, perchloric acid, phosphoric acid, hydrogen iodide, and the like. The preferable strong acid is either hydrochloric acid or methanesulfonic acid.

The biodegradable polymer can be any biocompatible and pharmaceutically acceptable polymers. The biodegradable polymers may be thermoplastic, which melts upon heating and solidifies upon cooling. The biodegradable polymers of the invention are substantially insoluble in aqueous or body fluid, but are capable of substantially dissolving or dispersing in a water-miscible organic solvent to form a solution or suspension. Upon contact with an aqueous fluid, the water-miscible organic solvent diffuses/dissipates from the inventive composition, which causes the coagulation of the polymer to form a gel, or solid matrix encapsulating the peptide agent. According to the present invention the biodegradable polymer may be a linear polymer, or a branched polymer, or a mixture of the two. Preferably, the polymer is a lactate-based polymer. The lactate-based polymer includes homopolymers of lactic acid or lactide monomers (poly (lactic acid) or polylactide, PLA), and copolymers of lactic acid (or lactide) with other monomers (for example, glycolic acid, glycolide (poly(lactide-co-glycolide), PLG or PLGA) and the like). Examples of the polymers suitable for the present composition includes, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), and copolymers, terpolymers, or combinations or mixtures therein. Lactic acid-based polymers, and copolymers of lactic acid and glycolic acid (PLGA), including poly(D,L-lactide-co-glycolide) and poly(L-lactide-co-glycolide) are preferably used in the present invention. In some embodiments, the PLGA polymers have weight average molecular weights of between about 2,000 to about 100,000 and monomer ratios of lactic acid to glycolic acid of between about 50:50 to about 100:0. The preferred polymers of the present invention are PLA with molecular weight of between 11,000 and about 18,000 for a controlled delivery of 6 months, and a PLGA with molecular weight of between 10,000 and 25,000 dalton having a lactide content of 80-90% for a 3- or 4-month delivery.

The pharmaceutically acceptable organic solvents may be selected from a group consisting of N-methyl-2-pyrrolidone, dimethylacetamide, methoxypolyethylene glycol, alkoxypolyethylene glycol, polyethylene glycol esters, glycofurol, glycerol formal, methyl acetate, ethyl acetate, methyl ethyl ketone, dimethylformamide, dimethyl sulfoxide, tetrahydrofuran, caprolactam, decylmethylsulfoxide, benzyl benzoate, ethyl benzoate, triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, ethyl lactate, propylene carbonate, ethylene carbonate, butyrolactone, and 1-dodecylazacyclo-heptan-2-one, and combinations thereof.

According to the present invention, one or more excipients may be incorporated in the inventive composition to achieve optimal delivery of the peptide agent. Suitable excipients may include release rate modifying agents, burst effect reducing materials, buffering materials, antioxidants, and the like.

According to the present invention, suitable release rate modifying agents include, but are not limited to, amphiphilic compounds or copolymers, such alkanecarboxylic acid, oleic acid, alkyl alcohol, polar lipids, surfactants, copolymers of polyethyleneglycol and polylactide or poly(lactide-co-glycolide), poloxamers, polyvinylpyrrolidone, polysorbates, and the like; esters of mono-, di-, and tricarboxylic acids, such as 2-ethoxyethyl acetate, benzyl benzoate, triethyl citrate, acetyl tributyl citrate, acetyl triethyl citrate, glycerol triacetate, di(n-butyl) sebecate, and the like; polyhydroxy alcohols, such as polyethylene glycol, sorbitol, and the like; fatty acids; triesters of glycerol, such as triglycerides, medium-chain triglycerides such as MIGLYOL 810, 812, 818, 829, 840, and the like. Mixtures of rate modifying agents can also be used in the polymer systems of the invention.

According to the present invention, suitable buffering agents include, but are not limited to, inorganic and organic salts including calcium carbonate, calcium hydroxide, calcium myristate; calcium oleate, calcium palmitate, calcium stearate, calcium phosphate, magnesium carbonate, magnesium hydroxide, magnesium phosphate, magnesium myristate, magnesium oleate, magnesium palmitate, magnesium stearate, zinc carbonate, zinc hydroxide, zinc myristate, zinc oleate, zinc palmitate, zinc stearate, zinc phosphate, and combinations thereof.

According to the present invention, suitable antioxidants include, but are not limited to, d-alpha tocopherol acetate, ascorbyl palmitate, butylated hydroxyanidole, butylated hydroxyanisole, butylatedhydroxyquinone, hydroxycomarin, butylated hydroxytoluene, ethyl gallate, propyl gallate, octyl gallate, lauryl gallate, propylhydroxybenzoate, trihydroxybutylrophenone, vitamin E, pegylated vitamin E or vitamin E-TPGS, and the like.

The present invention further provides methods of making and using such compositions. For example, a method of making such compositions comprising the neutralization of basic amine groups of peptide agents to form a beneficial salt to minimize or prevent the interaction/reaction of the basic amine group with the polymer; and the combination of the beneficial salt with other components and optionally one or more excipients. Preferably, the beneficial salt of the peptide agent is formed first, and then combined with the polymer dissolved in an organic solvent. Such compositions are physico-chemically stable prior to and during the fabrication process of a controlled delivery system such as microparticle formation or other implantable matrix formation. Preferably, such injectable compositions are physico-chemically stable during preparation, storage, and subsequent administration to a subject and form consistent and controlled release implants upon administration to a tissue site. The compositions of the present invention contain a biodegradable polymer, such that the duration of the release of the peptide is controlled over a period of up to 6 months.

The present invention further provides a kit for administration of the injectable composition to form a consistent and controlled release depot system, the kit comprises: a biodegradable polymer dissolved in a pharmaceutically acceptable solvent; a beneficial salt of a the LHRH agonist or antagonist formed with a strong acid dissolved or dispersed in the polymeric vehicle; and optionally one or more excipients. The uniform mixture of all the components is packaged into one container. Preferably, the container is a syringe. Accordingly, the present invention also provides a method comprising a step of filling a syringe with the composition to form a stable product in a ready-to-use configuration.

The present invention further provides a method for in-situ forming implant capable of functioning as a controlled release delivery system of the LHRH agonist or antagonist in a subject over a period of 1 month, 3 months, 4 months or 6 months. The LHRH agonist or antagonist is preferably incorporated into the in situ formed implant, and subsequently released into the surrounding tissue fluids and to the pertinent body tissue or organ as the polymer degrades. The method comprises: administration of the injectable compositions of the present invention to an implant site by any suitable method for applying a liquid, as for example, by means of a syringe, needle, cannula, catheter, pressure applicator, and the like.

BRIEF DESCRIPTION OF THE FIGURES

FIG. 9. In Vitro Release of Leuprolide mesylate with a molar ratio of 1.6:1 and 2:1 from PLGA5050 Formulations in PBS at pH 7.4 at 37° C.

DETAILED DESCRIPTION OF THE INVENTION

Figure 1:
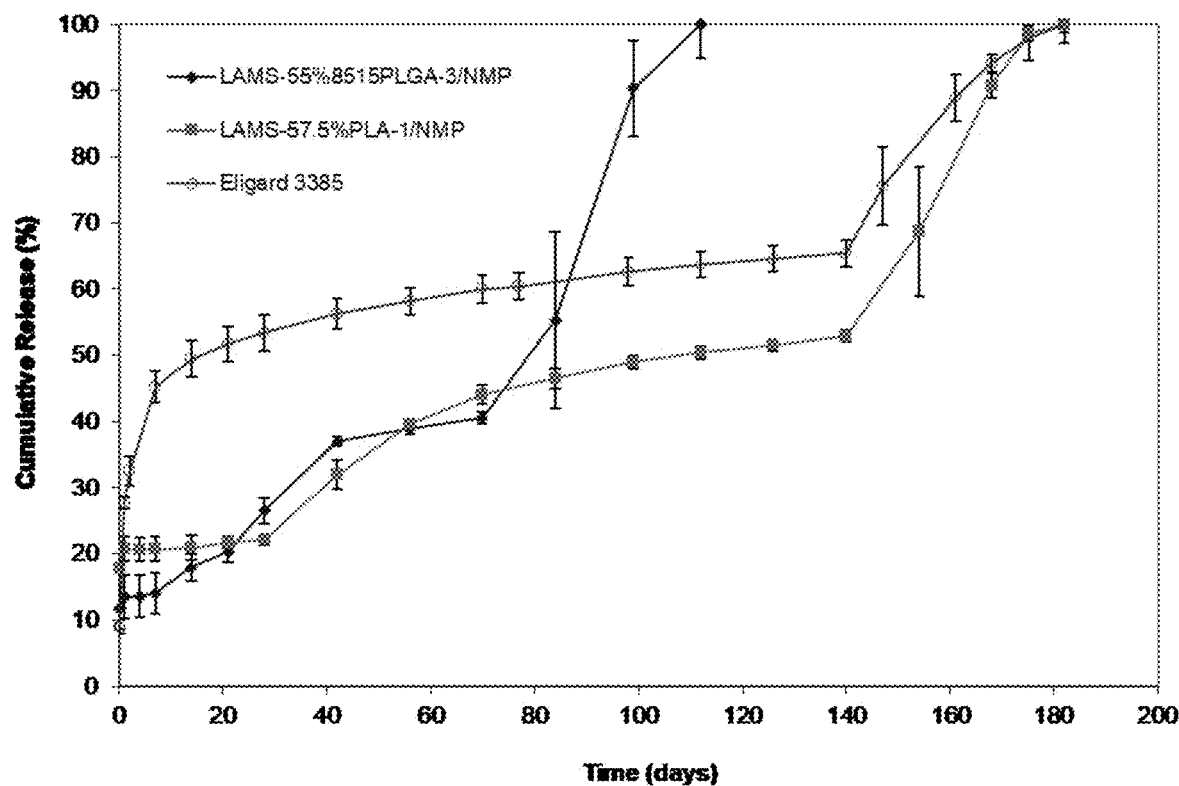
FIG. 1. In vitro release of leuprolide mesylate from different polymers compared with Eligard® 45 mg release FIG. 2. Mean Serum Concentration-Time Profiles of Leuprolide in Male Rats after a Single Subcutaneous Administration

The present invention provides a stabilized injectable biodegradable polymeric composition for forming an economical, practical, and efficient release delivery system for controlled release of leuprolide for a period of 1, 3, 4 or 6 months. The present invention also provides a method of manufacturing and a method of use thereof.

The compositions of the present invention comprise a) a beneficial salt of a LHRH agonist or antagonist formed with a strong acid that minimizes or prevents the interaction/reaction between the peptide agent and the polymer in an organic solution; b) a biodegradable polymer; c) a pharmaceutically acceptable organic solvent. According to the invention, the pharmaceutical composition may optionally include one or more excipients to achieve optimal delivery of the peptide agent. The injectable polymeric composition of the present invention may be a viscous or non-viscous liquid, gel or semisolid that moves as a fluid so that it may be injected using a syringe. The injectable polymeric composition may be pre-filled into one syringe to form a product kit in a ready-to-use configuration.

The compositions in accordance with the present invention comprise a) a mixture of a salt of a LHRH agonist or antagonist formed with a strong acid and a salt of a LHRH agonist or antagonist formed with a weak acid, wherein the molar ratio of strong acid to LHRH agonist or antagonist is from 1:1 to 2:1, wherein the composition does not contain excess acid in addition to the acids used to form the strong acid to LHRH agonist or antagonist; b) a biodegradable polymer; c) a pharmaceutically acceptable organic solvent, that when formulated together can deliver the LHRH agonist or antagonist over a 1-, 3-, 4- or 6-month period. According to the invention, the pharmaceutical composition may optionally include excipients to achieve optimal delivery of the peptide agent. The pharmaceutical composition may be a viscous or non-viscous liquid, gel or semisolid that moves as a fluid so that it may be injected using a syringe. The pharmaceutical composition may be pre-filled into one syringe to form a product in a ready-to-use configuration.

The controlled release delivery system of the present invention may be formed as an implantable polymeric matrix in vitro, or alternatively, it may be formed in-situ in the forms of a gel or a solid implant. When administered to a subject, the controlled release of the peptide can be sustained for a desired period of time depending upon the composition of the implant. With the selections of the biodegradable polymer and other components, the duration of the sustained release of the peptide agent can be controlled over a period of time from 1 month to 6 months.

The terms "a", "an" and "one", as used herein, are meant to be interpreted as "one or more" and "at least one."

The term "stabilized", as used herein, refers to a significant improvement in the stability of the components in the injectable polymeric composition, which is necessary to achieve a stable state required to develop a viable product. The term "stabilized injectable polymeric composition" as used herein means that the components, e.g., the polymer and the peptide agent, of the composition retains at least 80%, preferably at least 90%, of their original molecular weight, structure and/or biological activity during manufacturing and after storage for an extended time period, e.g., months to years, preferably more than 12 months, under appropriate conditions.

The term "controlled release delivery", as defined herein, is intended to refer to the delivery of a peptide agent in vivo over a desired, extended period of time following administration, preferably from one month to six months.

The term "peptide" or "peptide agent" as used herein is in a generic sense to include poly(amino acids) that are normally generally referred to as "peptides", "oligopeptides", and "polypeptides" or "proteins" which are used interchangeably herein. The term also includes peptide agent analogs, derivatives, acylated derivatives, glycosylated derivatives, pegylated derivatives, fusion proteins and the like. The "basic peptide agent" is a peptide which is basic in nature, arising from the presence of basic amino acids, for example arginine or lysine, or arising from the N-terminus of the peptide agent, or simply a peptide agent which contains at least one basic group, optionally in the presence of one or more acidic amino acid groups. The term also includes synthetic analogues of peptides, unnatural amino acids having basic functionality, or any other form of introduced basicity.

The term "peptide agent" is meant to include any peptide agents having diagnostic and/or therapeutic properties including, but not limited to, antimetabolic, antifungal, anti-inflammatory, antitumoral, antiinfectious, antibiotics, nutrient, agonist, and antagonist properties.

Specifically, the peptide agents of the invention may be any peptides capable of forming a beneficial salt with a strong acid, in particular a peptide agent containing an electron donor base group, such as a basic nitrogen atom, e.g. an amine, imine or ring nitrogen. The peptide agents preferably contain one or more exposed protonatable amine functionalities. Peptide agents useful in the preparation of the compositions of the present invention include, but are not limited to, oxytocin, vasopressin, adrenocorticotropic hormone (ACTH), epidermal growth factor (EGF), platelet-derived growth factor (PDGF), prolactin, luteinising hormone, luteinizing hormone releasing hormone (LHRH), LHRH agonists, LHRH antagonists, growth hormones (including human, porcine, and bovine), growth hormone releasing factor, insulin, erythropoietin (including all proteins with erythropoietic activity), somatostatin, glucagon, interleukin (which includes IL-2, IL-11, IL-12, etc.), interferon-alpha, interferon-beta, interferon-gamma, gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), exenatide, peptide YY (PYY), renin, bradykinin, bacitracins, polymyxins, colistins, tyrocidine, gram icidins, cyclosporins (which includes synthetic analogues and pharmacologically active fragments thereof), enzymes, cytokines, antibodies, vaccines, antibiotics, antibodies, glycoproteins, follicle stimulating hormone, kyotorphin, taftsin, thymopoietin, thymosin, thymostimulin, thymic humoral factor, serum thymic factor, colony stimulating factors, motilin, bombesin, dinorphin, neurotensin, cerulein, urokinase, kallikrein, substance P analogues and antagonists, angiotensin II, blood coagulation factor VII and IX, gramicidines, melanocyte stimulating hormone, thyroid hormone releasing hormone, thyroid stimulating hormone, pancreozymin, cholecystokinin, human placental lactogen, human chorionic gonadotrophin, protein synthesis stimulating peptide, gastric inhibitory peptide, vasoactive intestinal peptide, platelet derived growth factor, and synthetic analogues and modifications and pharmacologically-active fragments thereof.

The preferred peptide agents used herein include the peptide agents wherein the N-terminus is not a primary amine. For example, the N-terminus of the peptide agents may be a pyroglutamic acid, e.g., LHRH, and LHRH agonists such as leuprorelin, buserelin, gonadorelin, deslorelin, fertirelin, histrelin, lutrelin, goserelin, nafarelin, triptorelin, and the like. Alternatively, the N-terminal amine group may be capped or acylated, e.g., cetrorelix, enfuvirtide, thymosin α1, abarelix, and the like.

The preferred peptide agents used herein also include the peptide agents wherein the N-terminal primary amine is covalently modified with hydrophilic and/or lipophilic moieties such as through pegylation, acylation, and the like. The peptide agents used herein further include the peptide agents wherein the side chain primary amine(s) are covalently modified with hydrophilic and/or lipophilic moieties such as through pegylation, acylation, and the like. The preferred peptide agents used herein further include the peptide agents wherein both N-terminal primary amine and side chain primary amine groups are covalently modified simultaneously with hydrophilic and/or lipophilic moieties such as through pegylation, acylation, and the like.

The term "hydrophilic moiety" refers to any water-soluble linear or branched oligomer or polymer including, but not limited to, polyethylene glycol and polypropylene glycol and similar linear and branched polymers. Preferably, the molecular weight of the polymer ranges from about 500 daltons to about 50,000 daltons. Hydrophilic polymers for use in the present invention may have a reactive group incorporated for attachment to the peptide agent of interest through amine, carboxylic, hydroxyl, or thiol groups.

The term "pegylation" used herein refers to the covalent conjugation of a soluble polyethylene glycol to the peptide agents. Polyethylene glycol can be prepared according to standard protocols with one end capped as with a methoxy group and the other end activated for facile conjugation to active groups on peptide agents. For examples, various methods for preparing polyethylene glycols and their use for pegylations are described in the art: [e.g., Roberts M J, Bentley M D, Harris J M, Chemistry for peptide and protein PEGylation. Adv Drug Deliv Rev. 2002 Jun. 17; 54(4): 459-76. Veronese F M. Peptide and protein PEGylation: a review of problems and solutions. Biomaterials. 2001 March; 22(5): 405-17 and U.S. Pat. Nos. 6,113,906; 5,446,090; 5,880,255], which are all incorporated herein by reference.

The term "lipophilic moiety" refers to any molecules having a solubility in water at 20° C. less than 5 mg/ml, preferably less than 0.5 mg/ml, more preferably less than 0.1 mg/mL. Such a lipophilic moiety is preferably selected from $C_{2-39}$-alkyl, $C_{2-39}$-alkenyl, $C_{2-39}$-alkadienyl and steroidal residues. The term "$C_{2-39}$-alkyl, $C_{2-39}$-alkenyl, $C_{2-39}$-alkadienyl" are intended to cover straight chain and branched, preferably straight chain, saturated, monounsaturated and di-unsaturated hydrocarbon of 2-39 carbon atoms.

Introduction of a lipophilic moiety covalently to a peptide agent thereof leads to a lipophilically modified peptide that may have improved therapeutic effect comparing to the native molecule. This can be typically done by reacting an amine group in a peptide agent with an acid or other reactive groups in a lipophilic molecule. Alternatively, the conjugation between peptide agent and lipophilic molecule is accomplished through an additional moiety such as a bridge, spacer, or linkage moiety, which can be degradable or non-degradable. Some examples are disclosed in the prior art, [e.g., Hashimoto, M., et al., Pharmaceutical Research, 6:171-176 (1989), and Lindsay, D. G., et al., Biochemical J. 121:737-745 (1971), U.S. Pat. No. 5,693,609, WO95/07931, U.S. Pat. No. 5,750,497, and WO96/29342. WO98/08871, WO98/08872, and WO99/43708]. These disclosures are expressly incorporated herein by reference for describing lipophilically modified peptides and for enabling preparation of the same.

The term "strong acid", as defined herein, is meant to include any acids with a pKa less than 3, and preferably less than 0. The strong acids suitable for the present invention may be selected from, but not limited to, the group consisting of hydrochloric acid, hydrobromic acid, nitric acid, chromic acid, sulfuric acid, methanesulfonic acid, trifluromethane sulfonic acid, toluenesulfonic acid (p), trichloroacetic acid, dichloroacetic acid, bromoacetic acid, chloroacetic acid, cyanoacetic acid, 2-chloropropanoic acid, 2-oxobutanoic acid, 2-chlorobutanoic acid, 4-cyanobutanoic acid, pamoic acid, perchloric acid, phosphoric acid, hydrogen iodide, and the like.

The "strong acid" of the present invention also includes any organic sulfuric acids such as alkyl, aryl or alkylaryl sulfuric acids of 1-40 carbons, preferably less than 18 carbons, and more preferably less than 6 carbons, and organic sulfonic acids such as alkane, arylalkane, arene, or alkene sulfonic acids of 1-40 carbons, preferably less than 18 carbons, and more preferably less than 6 carbons.

The "weak acid", as defined herein, is meant to include any acids with a pKa greater than 3. The weak acids suitable for the present invention may be selected from, but not limited to, the group consisting of 1-hydroxy-2-naphthoic acid, 2-oxoglutaric acid, 4-acetamidobenzoic acid, 4-aminosalicylic acid, acetic acid, adipic acid, ascorbic acid (L), aspartic acid (L), benzoic acid, camphoric acid (+), capric acid (decanoic acid), caproic acid (hexanoic acid), caprylic acid (octanoic acid), carbonic acid, cinnamic acid, citric acid, formic acid, fumaric acid, galactaric acid, gentisic acid, glucoheptonic acid (D), gluconic acid (D), glucuronic acid (D), glutamic acid, glutaric acid, glycolic acid, hippuric acid, isobutyric acid, lactic acid (DL), lactobionic acid, lauric acid, maleic acid, malic acid (−L), malonic acid, mandelic acid (DL), oleic acid, oxalic acid, palmitic acid, proprionic acid, pyroglutamic acid (−L), salicylic acid, sebacic acid, stearic acid, succinic acid, tartaric acid (+L), thiocyanic acid, undecylenic acid, and the like.

The term "a beneficial salt of a peptide agent", as defined herein, is meant to include any salts of a peptide agent formed with a strong acid. The beneficial salts of peptide agents can be prepared by simple acid and base titration or neutralization. The beneficial salts of peptide agents can be prepared during its synthesis and purification processes. Alternatively, they can be prepared from peptide agent in the form of a free base. The free base is dissolved in a suitable liquid medium. This solution of the peptide agent is mixed with a solution of a strong acid to form the beneficial salts by removing the solvent through suitable means such as precipitation, filtration or lyophilization. If the peptide agent is in its common commercially available form of a salt formed with a weak acid (i.e., pKa>3) such as acetic acid, the weak acid can be replaced by a strong acid through common ion-exchange methods such as lyophilization, precipitation or other methods known in the art. For example, leuprolide acetate is dissolved in a suitable liquid medium, e.g., water. This solution of the peptide agent is mixed with an aqueous solution of a strong acid such as methanesulfonic acid. When the peptide acetate and a strong acid such as methanesulfonic acid are dissolved in water, the peptide tends to be associated with mesylate ion, as the stronger methanesulfonic acid displaces the weaker carboxylic acetic acid. The solvent and liberated acetic acid (or other weak but volatile carboxylic acid) may be removed under vacuum or lyophilization. Thus, the mixture solution is freeze-dried to remove water and weaker acid to form the beneficial salts. If the peptide agent is not stable under low pH, the beneficial salts of the peptide agent can be prepared through extensive dialysis against very low concentration of a strong acid.

The injectable polymeric compositions of the present invention may contain peptide agent in a range of 0.01 to 40% by weight. In general, the optimal drug loading depends upon the period of release desired and the potency of the peptide agent. Obviously, for peptide agent of low potency and longer period of release, higher levels of incorporation may be required.

The term "biodegradable" refers to a material that gradually decomposes, dissolves, hydrolyzes and/or erodes in situ. Generally, the "biodegradable polymers" herein are polymers that are hydrolyzable, and/or bioerode in situ primarily through hydrolysis and/or enzymolysis.

The term "biodegradable polymer" as used herein is meant to include any biocompatible and/or biodegradable synthetic and natural polymers that can be used in vivo, provided the polymer is at least substantially insoluble in aqueous medium or body fluid. The term "substantially insoluble" as used herein refers that the insolubility of the polymer must be sufficient to result in precipitation of the polymer in aqueous medium or body fluid. Preferably, the solubility of the polymers is less than 1% by weight, and more preferably less than 0.1%. When the polymer solution in a water miscible or dispersible organic solvent is mixed with an aqueous solution, the polymer will precipitate to form a solid or gelled matrix as the organic solvent dissipates. Suitable biodegradable polymers are disclosed, e.g., in U.S. Pat. Nos. 4,938,763; 5,278,201; 5,278,2012; 5,324,519; 5,702,716; 5,744,153; 5,990,194; and 6,773,714. Some non-limiting examples of the polymers are polylactides, polyglycolides, polycaprolactones, polydioxanones, polycarbonates, polyhydroxybutyrates, polyalkylene oxalates, polyanhydrides, polyesteramides, polyurethanes, polyacetals, polyorthocarbonates, polyphosphazenes, polyhydroxyvalerates, polyalkylene succinates, poly(malic acid), and polyorthoesters, and copolymers, block copolymers, branched copolymers, terpolymers and combinations and mixtures thereof.

The block copolymers include A-B-A block copolymers, B-A-B block copolymers, and/or A-B block copolymers and/or branched copolymers. The preferred block copolymers are those wherein the A block comprises a hydrophobic polymer and the B block comprises a hydrophilic polymer. Particularly, when using one of the aforementioned block copolymers, the most preferred polymeric matrices are defined where the A block is a biodegradable polymer selected from the group consisting of polylactides, polyglycolides, poly(lactide-co-glycolide)s, polyanhydrides, poly (ortho ester)s, polyetheresters, polycaprolactones, polyesteramides, poly(ε-caprolactone)s, poly(hydroxybutyric acid)s, and blends and copolymers thereof, and the B block is polyethylene glycol or monofunctionally derivatized polyethylene glycol such as methoxy polyethylene glycol. Many of these combinations may form acceptable thermal reversible gels.

Suitable molecular weights for polymers may be determined by a person of ordinary skill in the art. Factors that may be considered when determining molecular weights include desired polymer degradation rate, mechanical strength, and rate of dissolution of polymer in organic solvents. Typically, a suitable range of weight averaged molecular weights of polymers is of about 2,000 Daltons to about 100,000 Daltons with a polydispersity of from 1.1 to 2.5, preferably from 1.1 to 2.0, more preferably from 1.1 to 1.8, depending upon which polymer is selected for use, among other factors.

The injectable polymeric compositions of the present invention may contain biodegradable polymer in a range of 10% to 70% by weight. The viscosity of the injectable compositions of the invention depends on the molecular weight of the polymer and organic solvent used. Typically, when the same solvent is used, the higher the molecular weight and the concentration of the polymer, the higher the viscosity. Preferably the concentration of the polymer in the compositions is less than 70% by weight. More preferably concentration of the polymer in the compositions is between 30 to 60% by weight.

Poly(lactic acid), and copolymers of lactic acid and glycolic acid (PLGA), including poly(D,L-lactide-co-glycolide) and poly(L-lactide-co-glycolide) are preferably used in the present invention. The polymers (or thermoplastic polyesters) have monomer ratios of lactic acid to glycolic acid of between about 50:50 to about 100:0 and weight average molecular weights of between about 2,000 to about 100,000. The biodegradable thermoplastic polyesters can be prepared using the methods known in the art, e.g., polycondensation and ring-opening polymerization (e.g., U.S. Pat. Nos. 4,443,340; 5,242,910; 5,310,865, which are all incorporated herein by reference). The terminal groups of the poly(DL-lactide-co-glycolide) can either be hydroxyl, carboxylic, or ester depending upon the method of polymerization. The suitable polymers may include a monofunctional alcohol or a polyol residue and may not have a carboxylic acid terminus. Examples of monofunctional alcohols are methanol, ethanol, or 1-dodecanol. The polyol may be a diol, triol, tetraol, pentaol and hexaol including ethylene glycol, 1,6-hexanediol, polyethylene glycol, glycerol, saccharides, reduced saccharides such as sorbitol, and the like.

The copolymers of lactic acid and glycolic acid or lactide and glycolide include poly(D,L-lactide-co-glycolide) (PLGA) and poly(L-lactide-co-glycolide). The copolymers have monomer molar ratios of lactic acid to glycolic acid of between about 50:50 to about 100:0. When the molar ratio of 85:15 is used, it indicates the copolymer contains 80-90% of lactic acid or lactide and 10-20% of glycolic acid or glycolide. When the molar ratio of 75:25 is used, it indicates the copolymer contains 70-80% of lactic acid or lactide and 20-30% of glycolic acid or glycolide. When the molar ratio of 65:35 is used, it indicates the copolymer contains 60-70% of lactic acid or lactide and 30-40% of glycolic acid or glycolide. When the molar ratio of 50:50 is used, it indicates the copolymer contains 45-55% of lactic acid or lactide and 45-55% of glycolic acid or glycolide.

Many suitable PLGAs are available commercially, and the PLGAs of specific compositions can be readily prepared according to the prior art. The PLGAs of various monomer ratios and molecular weights are available from Boehringer-Ingelheim (Petersburg, Va., USA), Evonik (Birmingham, Ala., USA), DURECT Corporation (Pelham, Ala.).

The type, molecular weight, and amount of biodegradable polymer present in the compositions can influence the length of time in which the LHRH agonist or antagonist is released from the controlled release implant. The selection of the type, molecular weight, and amount of biodegradable polymer present in the compositions to achieve desired properties of the controlled release implant can be determined by simple experimentations. It was surprisingly found by the applicants of the present invention, that the salt of the peptide formed from a strong acid (e.g. mesylate) causes the biodegradable polymer to degrade faster once injected in an aqueous environment than a peptide of a salt formed from a weak acid (e.g. acetate), even though the stability of the formulation during storage is increased.

The term "pharmaceutically acceptable organic solvent" is meant to include any biocompatible organic solvents that are miscible or dispersible in aqueous or body fluid. The term "dispersible" means that the solvent partially soluble or miscible in water. Preferably, a single solvent or a mixture of solvents has a solubility or miscibility in water of greater than 0.1% by weight. More preferably, the solvent has a solubility or miscibility in water of greater than 3% by weight. Most preferably, the solvent has a solubility or miscibility in water of greater than 7% by weight. The suitable organic solvent should be able to diffuse into body fluid so that the liquid composition coagulates or solidifies. Single and/or mixture of such solvents can be employed; the suitability of such solvents can be determined readily by simple experimentations.

Examples of pharmaceutically acceptable organic solvent include, but not limited to, N-methyl-2-pyrrolidone, dimethylacetamide, methoxypolyethylene glycol, alkoxypolyethylene glycol, polyethylene glycol esters, glycofurol, glycerol formal, methyl acetate, ethyl acetate, methyl ethyl ketone, dimethylformamide, dimethyl sulfoxide, tetrahydrofuran, caprolactam, decylmethylsulfoxide, benzyl benzoate, ethyl benzoate, triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, ethyl lactate, propylene carbonate, ethylene carbonate, butyrolactone, and 1-dodecylazacyclo-heptan-2-one, and combinations thereof.

The solubility of the biodegradable polymers in various pharmaceutically acceptable organic solvents will differ depending upon the characteristics of the polymers and their compatibility with various solvents. Thus, the same polymer will not be soluble to the same extent in different solvents. For example, PLGA has a much higher solubility in N-methyl-2-pyrrolidone (NMP) than that in triacetin. However, when PLGA solution in NMP is in contact with aqueous solution, NMP will dissipate very rapidly to form a solid polymer matrix due to its high water miscibility. The fast diffusion rate of the solvent may result in a solid implant quickly, however, it may also lead to a high initial burst release. When PLGA solution in triacetin is in contact with aqueous solution, triacetin will dissipate very slowly due to its low water miscibility. The slow diffusion rate of the solvent may take a long time to transform from a viscous liquid to a solid matrix. There may be an optimum balance at which the solvent diffuses out and the coagulation of the polymer to encapsulate peptide agents. Therefore, it may be advantageous to combine different solvents to obtain a desirable delivery system. The solvents of low and high water miscibility may be combined to improve the solubility of the polymer, modify the viscosity of the composition, optimize the diffusion rate, and reduce the initial burst release, The injectable polymeric compositions of the present invention typically contain an organic solvent in a range of 30% to 80% by weight. The viscosity of the injectable compositions of the invention depends on the molecular weight of the polymer and organic solvent used. Preferably the concentration of the polymer in the compositions is less than 70% by weight. More preferably concentration of the polymer in solutions is between 30 to 60% by weight.

In one preferred embodiment of the present invention, the liquid composition can be used to formulate a controlled release delivery system for leuprolide hydrochloride or leuprolide mesylate. In such an embodiment, the biodegradable thermoplastic polyester can preferably be 85/15 poly(DL-lactide-co-glycolide) containing a hydroxyl terminal group and a lauryl ester terminus; can be present in about 30% to about 60% of the composition by weight; and can have an average molecular weight of about 8,000 to about 50,000.

In another preferred embodiment of the present invention, the liquid composition can be used to formulate a controlled release delivery system for leuprolide mesylate. In such an embodiment, the biodegradable thermoplastic polyester can preferably be 85/15 poly (DL-lactide-co-glycolide) containing two hydroxyl terminal groups; can be present in about 30% to about 60% of the composition by weight; and can have an average molecular weight of about 8,000 to about 50,000, preferably from 11,000 to 25,000 daltons.

In still another preferred embodiment of the present invention, the liquid composition can be used to formulate a controlled release delivery system for leuprolide mesylate. In such an embodiment, the biodegradable thermoplastic polyester can preferably be 85/15 poly (DL-lactide-co-glycolide) containing a carboxylic acid terminal groups; can be present in about 30% to about 60% of the composition by weight; and can have an average molecular weight of about 8,000 to about 50,000, preferably from 11,000 to 25,000 daltons.

In still another preferred embodiment of the present invention, the composition can be used to formulate a controlled release delivery system of leuprolide mesylate. In such an embodiment, the biodegradable polymer can preferably be 100/0 poly (DL-lactide) with/without carboxylic acid terminal groups; can be present in about 40% to about 60% of the composition by weight; and can have an average molecular weight of about 8,000 to about 50,000, preferably from 11,000 to 25,000 daltons. When formulated with a pharmaceutically acceptable organic solvent, such as NMP, the formulation has improved stability over leuprolide acetate, and can deliver leuprolide for a period of 6 months.

In still another preferred embodiment of the present invention, the composition can be used to formulate a controlled release delivery system of leuprolide mesylate. In such an embodiment, the biodegradable polymer can preferably be 85/15 poly (DL-lactide-co-glycolide) with/without carboxylic acid terminal groups; can be present in about 40% to about 60% of the composition by weight; and can have an average molecular weight of about 8,000 to about 50,000, preferably from 11,000 to 25,000 daltons. When formulated with a pharmaceutically acceptable organic solvent, such as NMP, the formulation has improved stability over leuprolide acetate, and can deliver leuprolide for a period of 3 or 4 months.

The term "excipients" as used herein is meant to include any useful ingredient in the composition aside from the peptide agent or the biodegradable polymers used to form the composition. Suitable excipients include release rate modifying agents, burst effect reducing materials, buffering materials, antioxidants, and the like.

According to the present invention, suitable release rate modifying agents include, but not limited to, amphiphilic compounds or copolymers, such alkanecarboxylic acid, oleic acid, alkyl alcohol, polar lipids, surfactants, copolymers of polyethyleneglycol and polylactide or poly(lactide-co-glycolide), benzyl benzoate, poloxamers, polyvinylpyrrolidone, polysorbates, and the like; esters of mono-, di-, and tricarboxylic acids, such as 2-ethoxyethyl acetate, triethyl citrate, acetyl tributyl citrate, acetyl triethyl citrate, glycerol triacetate, di(n-butyl) sebecate, and the like; polyhydroxy alcohols, such as polyethylene glycol, sorbitol, and the like; fatty acids; triesters of glycerol, such as triglycerides, medium-chain triglycerides such as MIGLYOL 810, 812, 818, 829, 840, and the like. Mixtures of rate modifying agents can also be used in the polymer systems of the invention.

The release rate modifying agents may be present in the injectable polymeric composition in an amount effective to reduce the initial burst of peptide agent released from the polymeric composition during the first 24 hours after implantation. Preferably, the polymeric composition includes about 1% to about 50% by weight, more preferably about 2% to about 20% by weight of the release rate modifying agents.

According to the present invention, suitable buffering agents include, but are not limited to, inorganic and organic salts including calcium carbonate, calcium hydroxide, calcium myristate; calcium oleate, calcium palmitate, calcium stearate, calcium phosphate, magnesium carbonate, magnesium hydroxide, magnesium phosphate, magnesium myristate, magnesium oleate, magnesium palmitate, magnesium stearate, zinc carbonate, zinc hydroxide, zinc myristate, zinc oleate, zinc palmitate, zinc stearate, zinc phosphate, and combinations thereof.

The buffering agents may be present in the injectable polymeric composition in an amount effective to stabilize the pH within the implants during the degradation process. Preferably, the polymeric composition includes about 1 wt % to about 30 wt %, more preferably about 2 wt % to about 15 wt % of the buffering agents.

According to the present invention, suitable antioxidants include, but are not limited to, d-alpha tocopherol acetate, ascorbyl palmitate, butylated hydroxyanidole, butylated hydroxyanisole, butylatedhydroxyquinone, hydroxycomarin, butylated hydroxytoluene, ethyl gallate, propyl gallate, octyl gallate, lauryl gallate, propylhydroxybenzoate, trihydroxybutylrophenone, vitamin E, pegylated vitamin E or vitamin E-TPGS, and the like.

The antioxidants may be present in the injectable polymeric composition in an amount effective to scavenge any radicals or peroxides generated within the implants. Preferably, the polymeric composition includes about 1 wt % to about 30 wt %, more preferably about 3 wt % to about 15 wt % of the antioxidants.

In one aspect the present invention provides a stabilized injectable biodegradable polymeric composition for forming an economical, practical, and efficient controlled release delivery system for a LHRH agonist or antagonist comprises a) a beneficial salt of a LHRH agonist or antagonist formed with a strong acid which minimizes or prevents the interaction/reaction between the peptide and the polymer in an organic solution; b) a biodegradable polymer; c) a pharmaceutically acceptable organic solvent; and d) optionally one or more excipients to achieve optimal delivery of the peptide agent. Preferably, the injectable composition is packaged into a kit comprising a step to fill the composition into a syringe in a ready-to-use configuration. The composition in the kit is stable for a reasonable period of time, preferably at least one year, to have a suitable storage shelf-life under controlled storage conditions. The composition is preferably injected into a subject to form in situ an implant, from which the peptide agent is released in a therapeutic effective amount over a desired, extended period of time.

In another aspect the present invention provides a stabilized injectable biodegradable polymeric composition having a selected release duration in vitro and in vivo for a LHRH agonist or antagonist comprises a) a mixture of a beneficial salt of a LHRH agonist or antagonist formed with a strong acid and a salt of a LHRH agonist or antagonist formed with a weak acid; b) a biodegradable polymer; c) a pharmaceutically acceptable organic solvent to achieve optimal delivery of the peptide agent. A desired release duration for a LHRH agonist or antagonist can be achieved by selecting an appropriate ratio of the mixture of a beneficial salt of a LHRH agonist or antagonist formed with a strong acid to a salt of a LHRH agonist or antagonist formed with a weak acid. The ratios of the mixture of a beneficial salt of a LHRH agonist or antagonist formed with a strong acid to a salt of a LHRH agonist or antagonist formed with a weak acid range from 1:0 to 0:1. The preferred ratios may be any of 1:0, 1:1, 3:2, 7:3, 4:1, 17:3, 9:1, 10:1, 11:1, 12:1, 14:1, 16:1, 18:1, 19:1, 20:1, 30:1, 40:1 and 50:1. The release duration for a LHRH agonist or antagonist can be from 1 month to 9 months, preferably 3 months, 4 months, or 6 months.

A LHRH agonist or antagonist can form a salt with either a strong acid or a weak acid. The salts used in the invention do not contain excess acid in addition to the acid used to form the salt of the LHRH agonist or antagonist. Due to the weak base and weak acid may not form ion pairs completely, thus, some weak base groups may exist in free base form. Therefore, in some cases, acids may exist less than the acids used to form the salt of the LHRH agonist or antagonist stoichiometrically.

The stabilized injectable biodegradable polymeric composition of the present invention can be prepared by appropriately combining a beneficial salt of a LHRH agonist or antagonist, a biodegradable polymer, a pharmaceutically acceptable organic solvent, and an optional excipient. The composition for administration may be conveniently presented in dosage unit form and may be prepared by any of the methods known in the art of pharmacy. One preferred method of preparing the composition of the present invention is to dissolve a biodegradable polymer and/or an excipient in a pharmaceutically acceptable organic solvent to obtain a uniform polymer solution/suspension first. Then the beneficial salt of a LHRH agonist or antagonist is added to this solution/suspension. The components are thoroughly mixed using any proper means to obtain a uniform solution or suspension. Then an appropriate amount of the solution or suspension is transferred into a syringe to obtain a ready-to-use product.

The level of incorporation of the beneficial salt and polymer in the composition of the invention will naturally vary, depending upon the potency of the LHRH agonist or antagonist component, the period of time over which delivery of the agent is desired, the solubility of the polymer in the solvent, and the volume and viscosity of the injectable composition which is desired to administer.

In certain preferred embodiments of the present invention, the injectable biodegradable polymeric composition for forming an economical, practical, and efficient controlled release delivery system for LHRH agonists or antagonists contains about 0.01% to 40% of the beneficial salt of a LHRH agonist or antagonist and about 10% to 70% of a poly(lactide-co-glycolide) polymer. The composition further contains about 30% to 70% of a pharmaceutically acceptable organic solvent.

In a preferred embodiment of the present invention, the composition further contains about 1% to 40% of a suitable excipient including release rate modifying agents, burst effect reducing materials, buffering materials, antioxidants, tissue transporting agents and the like as defined above.

According to the present invention, the injectable composition is transferred into a sterile container suitable for injection administration, e.g., a syringe. The container is packaged for storage and the components of the composition retains at least 80%, preferably 90%, of their original molecular weight, structure and/or biological activity during manufacturing and storage processes or prior to administration to a subject such as an animal or human.

Thus, according to the present invention, the stabilized compositions can be administered to a subject where controlled release delivery of a peptide agent is desired. As used herein, the term "subject" is intended to include warm-blooded animals, preferably mammals, most preferably humans.

As used herein, the term "administered to a subject" is intended to refer to dispensing, delivering or applying a composition (e.g., pharmaceutical formulation) to a subject by any suitable route for delivery of the composition to the desired location in the subject. Preferably, the composition of the present invention can be administered by injection and/or implantation subcutaneously, intramuscularly, intraperitoneally, or intradermally to provide the desired dosage based on the known parameters for treatment of the various medical conditions with the peptide agent.

The term "controlled release delivery", as defined herein, is intended to refer to continual delivery of a peptide agent in vivo over a period of time following administration, preferably from at least several weeks to one year. Sustained controlled release delivery of the agent can be demonstrated by, for example, the continued therapeutic effect of the agent over time (e.g., for an LHRH analogue, sustained delivery of the analogue can be demonstrated by continued suppression of testosterone synthesis over time). Alternatively, sustained delivery of the peptide agent may be demonstrated by detecting the presence of the agent in vivo over time.

The amount of the injectable composition administered will typically depend upon the desired properties of the controlled release implant. For example, the amount of the injectable composition can influence the length of time in which the peptide agent is released from the controlled release implant.

In a preferred embodiment, the volume of the injectable polymeric composition of the present invention to be injected to a subject range from 0.1 mL to 2.0 mL; preferably from 0.2 mL to 1.0 mL; and more preferably from 0.3 mL to 0.5 mL.

The present invention further provides a method for in situ forming an implant in a subject comprising administering to a subject an effective amount of the injectable composition comprising: a) a beneficial salt of a LHRH agonist or antagonist formed with a strong acid which minimizes or prevents the interaction/reaction between the peptide agent and the polymer in an organic solution; b) a biodegradable polymer; c) a pharmaceutically acceptable organic solvent; and d) optionally one or more excipients to achieve optimal delivery of the LHRH agonist or antagonist; and allowing the solvent to dissipate into the surrounding aqueous environment to transform the liquid composition into a depot by phase separation. The depot may be a viscous gel, a semi-solid, or a solid matrix. The depot may also be porous or non-porous. The depot serves as the delivery system from which the LHRH agonist or antagonist is released over a desired and extended period of time.

In another preferred embodiment, the injectable composition of the present invention may be administered to fit into a body cavity to form a depot system. Such cavities include the cavities created after a surgery or natural body cavity such as vagina, anus, and the like.

In another aspect, the present invention provides a stabilized liquid biodegradable polymeric composition for forming an economical, practical, and efficient controlled release delivery system for LHRH agonists or antagonists comprising a) a beneficial salt of a LHRH agonist or antagonist formed with a strong acid which minimizes or prevents the interaction/reaction between the LHRH agonist or antagonist and the polymer in an organic solution; b) a biodegradable polymer; c) an organic solvent; and d) optionally one or more excipients to achieve optimal delivery of the peptide agent. The liquid biodegradable polymeric composition may be fabricated into implantable polymeric matrices. Wherein the liquid biodegradable polymeric composition retains at least 90%, preferably 95%, of their original molecular weight, structure and/or biological activity before and during the fabrication process.

As used herein, the term of "implantable polymeric matrices" is intended to include particles, films, pellets, cylinders, discs, microcapsules, microspheres, nanospheres, microparticles, wafers, and other known polymeric configurations used for drug delivery.

Methods for forming various pharmaceutically acceptable polymer carriers are well known in the art. For examples, various methods and materials are described in U.S. Pat. Nos. 6,410,044; 5,698,213; 6,312,679; 5,410,016; 5,529,914; 5,501,863; and PCT Publication No. WO 93/16687; U.S. Pat. Nos. 4,938,763; 5,278,201; 5,278,202; EP 0,058,481; which are all incorporated herein by reference.

According to the present invention, the implantable polymeric matrices in the form of microspheres are produced by encapsulating the beneficial salt of LHRH agonists or antagonists into the polymer. The beneficial salt of LHRH agonists or antagonists can be encapsulated using various biocompatible and/or biodegradable polymers having unique properties that are suitable for delivery to different biological environments or for effecting specific functions. The rate of dissolution and, therefore, delivery of LHRH agonist or antagonist is determined by the particular encapsulation technique, polymer composition, polymer cross-linking, polymer thickness, polymer solubility, size and solubility of biologically active compound/polyanion complex.

The beneficial salts of LHRH agonists or antagonists to be encapsulated are dissolved or suspended in a polymer solution in an organic solvent. The polymer solution must be concentrated enough to completely coat the beneficial salt after they are added to the solution. Such an amount is one that provides a weight ratio of the beneficial salt to polymer between about 0.01 and about 50, preferably between about 0.1 and about 30. The beneficial salt of LHRH agonist or antagonist should be kept suspended and not allowed to aggregate as they are coated by contact with the polymer.

A polymer solution of the beneficial salts of LHRH agonist or antagonist can therefore be subjected to a variety of microencapsulation techniques including spray drying, spray congealing, emulsion, and solvent evaporation emulsion.

According to one embodiment of the invention, the beneficial salt of LHRH agonists or antagonists is dissolved or suspended in a polymer solution in an organic solvent. The solution or suspension is transferred to a larger volume of an aqueous solution containing an emulsifier. In the aqueous solution, the organic phase is emulsified, where the organic solvent evaporates or diffuses away from the polymer. The solidified polymer encapsulates the beneficial salt of LHRH agonists or antagonists to form a polymer matrix. The emulsifier helps to reduce the interfacial surface tension between the various phases of matter in the system during the hardening phase of the process. Alternatively, if the encapsulating polymer has some inherent surface activity, there may be no need for addition of a separate surface-active agent.

Emulsifiers useful to prepare encapsulated the beneficial salt of LHRH agonists or antagonists according to the present invention include poloxamers and polyvinyl alcohol as exemplified herein, surfactants and other surface active compounds which can reduce the surface tension between the polymer encapsulated beneficial salt of LHRH agonists or antagonists and the solution.

Organic solvents useful to prepare the microspheres of the present invention, except for those disclosed above, also include acetic acid, acetone, methylene chloride, ethyl acetate, chloroform and other non-toxic solvents that will depend on the properties of the polymer. Solvents should be chosen to dissolve the polymer and are ultimately non-toxic.

Thus, according to the present invention, these implantable polymeric matrices can be administered to a subject where sustained controlled release delivery of a LHRH agonist or antagonist is desired. Preferably, the implantable polymeric matrices of the invention can be administered by injection and/or implantation subcutaneously, intramuscularly, intraperitoneally, or intradermally to provide the desired dosage based on the known parameters for treatment of the various medical conditions with the LHRH agonist or antagonist.

All books, articles and patents referenced herein are fully incorporated by reference.

EXAMPLES

The following examples illustrate the compositions and methods of the present invention. The following examples should not be considered as limitations, but should merely teach how to make the useful controlled release drug delivery compositions.

Example 1: Stability of Peptide Agent and Biodegradable Polymer in Injectable Polymeric Compositions Poly(DL-lactide-co-glycolide) (PLGA) of an 85/15 ratio of lactide to glycolide (DLPLG85/15, IV: 0.28) with a lauryl ester end group was dissolved in N-methyl-2-pyrrolidone (NMP) to give a 50% solution by weight. The leuprolide salts were mixed with the PLGA solution in NMP to give a uniform injectable composition at ratios shown in the Table 1. The injectable compositions were filled into 1.2 mL polypropylene syringes with luer-lock tips. Then the pre-filled syringes were sealed using luer-lock caps. The capped syringes were packaged in a container and sealed in a plastic bag under vacuum and then stored at 4° C. and room temperature (~22° C.) for up to 18 months. The injectable composition was sampled at 24 h, 1, 2, 3, 6, 12, and 18-month time points. Purity of leuprolide in the sample was determined by HPLC. Molecular weight of the polymer was determined by gel permeation chromatography (GPC) using polystyrene standards with known molecular weights.

TABLE 1

Injectable polymeric formulations tested

| Samples | Leuprolide Salt (mg) | DLPLG8515/NMP (mg) | Drug load (%, w/w) |
|---|---|---|---|
| Blank | 0 | 1000 | 0 |

TABLE 1-continued

Injectable polymeric formulations tested

| Samples | Leuprolide Salt (mg) | DLPLG8515/NMP (mg) | Drug load (%, w/w) |
|---|---|---|---|
| LA-Ac | 50 | 890 | 5.3 |
| LA-MS | 54 | 960 | 5.3 |
| LA-HCl-1 | 106 | 940 | 10.1 |
| LA-HCl-2 | 41 | 730 | 5.3 |

It was surprisingly found that the use of hydrochloride and mesylate salts of leuprolide instead of acetate significantly reduced the degradation of leuprolide and polymer in PLGA solutions in NMP at both 4° C. and room temperature over time. Tables 2 and 3 showed the degradation of leuprolide in PLGA solutions in NMP at 4° C. and room temperature over time respectively. At 4° C., up to 23% of leuprolide was degraded in the polymeric composition containing leuprolide acetate, while less than 2% of leuprolide was degraded for those formulations containing leuprolide hydrochloride and leuprolide mesylate after 18 months. At room temperature, more than 35% degradation of leuprolide was observed for leuprolide acetate formulations, while only about 11% for leuprolide hydrochloride and leuprolide mesylate formulations after 12 months.

TABLE 2

Stability of Leuprolide in PLGA/NMP Formulation at 4° C.

| Time (M) | LA-AC | LA-HCl-1 | LA-MS |
|---|---|---|---|
| 0 | 100.0 | 100.0 | 100.0 |
| 1 | 89.3 | 100.0 | 100.0 |
| 3 | 100.0 | 100.0 | 100.0 |
| 6 | 94.1 | 100.0 | 100.0 |
| 12 | 88.2 | 100.0 | 98.9 |
| 18 | 76.9 | 98.5 | 98.3 |

TABLE 3

Stability of Leuprolide in PLGA/NMP Formulation at RT

| Time (M) | LA-AC | LA-HCl-1 | LA-HCl-2 | LA-MS |
|---|---|---|---|---|
| 0 | 100 | 100 | 100 | 100 |
| 1 | 75 | 99 | 100 | 95 |
| 2 | 78 | 98 | 97 | 97 |
| 3 | 86 | 100 | 100 | 100 |
| 6 | 87 | 99 | 100 | 99 |
| 12 | 65 | 89 | 89 | 89 |

Table 4 and 5 showed the changes of molecular weight of the polymer in different formulations. Comparing to blank control, the molecular weight of PLGA in leuprolide acetate formulation decreased more than 10% at 4° C. and more than 90% at room temperature after 6 months. The molecular weight of PLGA in leuprolide hydrochloride and leuprolide mesylate formulations was the same as that of the blank control at both 4° C. and RT even after 12 months. However, after 12 months, more than 90% of the polymer from both blank control and leuprolide hydrochloride and leuprolide mesylate formulations was degraded. The results indicate that the salts of leuprolide formed with strong acid such as HCl and methanesulfonic acid completely prevent the interaction/reaction between the peptide and PLGA in solution. While the weak acid such as acetic acid does not prevent the deleterious interaction/reaction between the peptide and PLGA in solution. Thus, the improvement of the stability of the formulation by using the salt of the peptide formed with a strong acid enables the manufacturing of a ready-to-use injectable composition with a satisfactory storage stability of at least one year.

TABLE 4

Molecular Weight of PLGA in Different Formulations over time at 4° C.

| Time (M) | Blank | LA-AC | LA-HCl-1 | LA-MS |
|---|---|---|---|---|
| 0 | 24655 | 23842 | 24369 | 24556 |
| 1 | 25214 | 24282 | 25203 | 24574 |
| 3 | 24567 | 22775 | 24833 | 24833 |
| 6 | 23935 | 21957 | 24661 | 24034 |
| 12 | 23905 | 18906 | 23837 | 23393 |
| 18 | 22178 | 16107 | 22802 | 22227 |

TABLE 5

Molecular Weight of PLGA in Different Formulations over time at room temperature

| Time (M) | Blank | LA-AC | LA-HCl-1 | LA-HCl-2 | LA-MS |
|---|---|---|---|---|---|
| 0 | 24655.0 | 24282 | 24567 | 24468 | 24468 |
| 1 | 24282.2 | 20526 | 25022 | 25022 | 24832 |
| 2 | 22969.3 | 15459 | 23230 | 23230 | 22969 |
| 3 | 23227.7 | 11073 | 23228 | 23311 | 21872 |
| 6 | ND | 3409 | 18998 | 17952 | 15114 |
| 12 | 3112.3 | 380 | 4236 | 3388 | 2531 |

Example 2: Delivery of Leuprolide Over 6 Months

Eligard® 45 mg can deliver leuprolide acetate for 6 months. The product is supplied in 2 separate syringes with the leuprolide acetate in one syringe and the polymer solution in the other. The two are mixed immediately prior to injection. The polymer solution contains a 50% 8515PLGA polymer solution in NMP. The molecular weight of the polymer is about 20 k dalton. A comparable formulation was made using leuprolide mesylate having a molar ratio of mesylate to leuprolide of 1.55:1 (LAMS(1.55)) with a similar 8515PLGA polymer. This polymer had a molecular weight around 20 k dalton as well and a polydispersity index (PDI) of 1.7. The leuprolide mesylate was prepared from leuprolide acetate by ion exchange lyophilization process and contains a small amount of acetate. The formulation was mixed and stored in a single syringe. Another formulation was made with LAMS using a PLA polymer with a molecular weight of 15 k dalton (PLA-1) and a polydispersity index (PDI) of 1.8. This formulation was also mixed and stored in a single syringe. These formulations, along with an Eligard® 45 mg (Lot #3385) were then tested in vitro in PBS at pH 7.4 and 37° C. The release sample was taken at predefined time points and analyzed by HPLC. FIG. 1 shows the release of leuprolide over time.

The release of leuprolide from the 8515PLGA-3 polymer formulation was complete by 112 days. The pellets were also completely degraded from the release media at this time. The release of leuprolide from the PLA-1 and Eligard® 45 mg pellets continued until about 180 days. The difference in release duration is unexpected since using the 8515PLGA polymer like the one in the Eligard® 45 mg formulation, the implant does not last as long with LAMS in the formulation. Thus, a PLA polymer is needed in order to have a comparable release to the Eligard® 45 mg formulation and last for 6 months. Surprisingly, even though the formulation with LAMS is more stable during storage than formulations with leuprolide acetate, the polymer molecular weight degrades faster in the release media. Another surprising result was the lower initial release of LAMS from the PLA-1 compared to the release of leuprolide from Eligard® 45 mg.

Example 3: Delivery of Leuprolide In Vivo Over 6 Months

The objectives of this study were to characterize the pharmacokinetics of depot formulations containing leuprolide mesylate following a single subcutaneous dose in male rats for a period of 7 months and to investigate the effect of different polymers and activity of the formulations following SC administration in rats. Eligard® 45 mg served as reference drug. The release of leuprolide (LA) was determined by analyzing the serum concentrations of LA as a function of time after SC administration.

Figure 2:
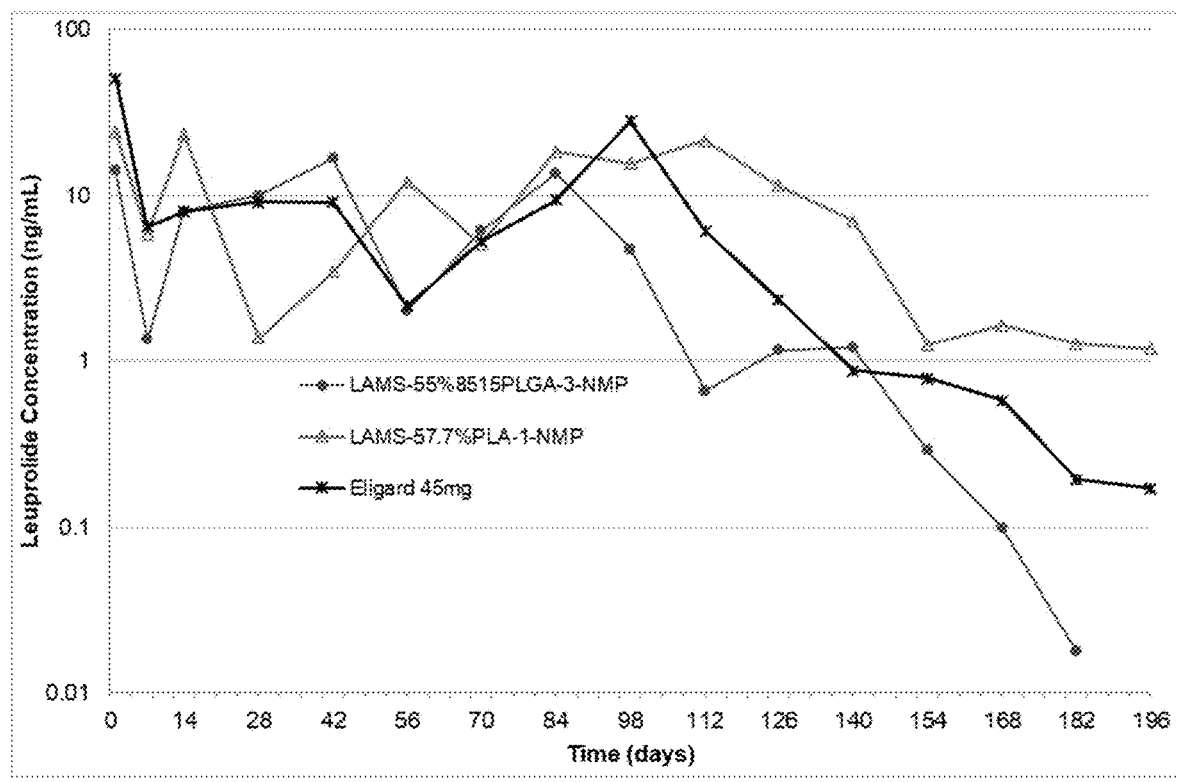

Male rats were divided into groups (6/group) and received the following leuprolide mesylate (LAMS1.55) formulations. 55.2% 8515PLGA-3/44.8% NMP (irradiation dose 25 kGy), 57.6% PLA-1/42.4% NMP (irradiation dose 25 kGy), or a reference drug, Eligard® 45 mg. The 8515PLGA-3 polymer had a molecular weight similar to the molecular weight of the Eligard® 45 mg (20 k) and the PLA-1 polymer had a molecular weight of 15 k. Blood samples were collected prior and after dosing up to Day 196. FIG. 2 shows the leuprolide concentration over time. The leuprolide concentrations for all formulations is similar up to about 140 days. Then the concentration of leuprolide begins to drop dramatically for the 8515PLGA-3 formulation until it is not detectable at 196 days.

The implants from this study were retrieved and analyzed for leuprolide content and polymer molecular weight. Table 6 shows the amount of leuprolide left and the percent molecular weight decrease.

TABLE 6

Implant analysis

| Formulation | % MW Reduction | % Leuprolide Remaining |
|---|---|---|
| LAMS-55% 8515PLGA-3/NMP | — | — |
| LAMS-57.5% PLA-1/NMP | 72.6 | 2.1 |
| Eligard ® 45 mg | 73.0 | 0.4 |

No implants were found in the animals that received the LAMS with 8515PLGA-3 formulation. This is consistent with the serum leuprolide concentrations, which showed a steep drop in leuprolide concentrations at later times to where it was below the detectable limit at 196 days.

The molecular weight degradation was similar for the LAMS-PLA-1 formulation and Eligard® 45 mg formulation, with about 73% reduction of the polymer molecular weight. There was still some leuprolide remaining, but the release was almost complete with about 2% remaining in the LAMS-PLA-1 formulation and less than 1% for the Eligard® 45 mg formulation. Thus, it is necessary to use a PLA polymer with molecular weight around 15 k when formulating with LAMS in order to have a 6 month in vivo release, similar to the release of Eligard® 45 mg. This result is unexpected. Despite the formulation being more stable during storage, once injected, LAMS with a similar polymer solution as Eligard® 45 mg, degrades faster and cannot sustain the release for 6 months as Eligard® 45 mg, which uses leuprolide acetate in the formulation.

Example 4: Evaluation of the PK/PD Profiles of Formulations Containing Leuprolide Mesylate Administered Subcutaneously in Male Rats The objective of this study was to characterize the pharmacokinetics (PK) of leuprolide after a single subcutaneous injection of different doses of leuprolide mesylate in a polylactide (PLA) solution in N-methylpyrrolidone (NMP) to male Sprague-Dawley rats. The leuprolide mesylate was prepared from leuprolide formate by column ion exchange. The resulting product has a molar ratio of methanesulfonic acid to leuprolide in a range from 1.5:1 to 1.8:1. The PLA in the formulation has a weighted average molecular weight ranging from 11,000 to 18,000 daltons and a polydispersity of 1.8 as determined by GPC using polystyrene standards in THF. The PLA polymer used was manufactured with a dodecanol (or lauryl alcohol) as an initiator, resulting in the PLA polymer with one hydroxyl end group at one end and one dodecyl ester group at the other end. The test article is designed to deliver leuprolide for a period of 6 months. The reference article Eligard® 45 mg, a 6 month sustained release formulation of leuprolide acetate, was used as a reference control. The release of leuprolide was determined by analyzing the serum concentrations of leuprolide as a function of time after SC administration, while the activity of leuprolide in various formulations was evaluated by the suppression of serum testosterone levels over time.

Study Design

For the PK study, three different dose levels of the test article leuprolide mesylate having a molar ratio of methanesulfonic acid to leuprolide in a range from 1.5:1 to 1.8:1 and Eligard® 45 mg were administered to a total of 80 male rats in three dosing groups of Test article (Groups 3, 4, and 5) and reference article-treated group (Group 6) at single dose levels of 6.8 mg, 20.3 mg, 33.8 mg and 30 mg, respectively. Sham and vehicle control groups (Groups 1, 2) for the PK study contained a total of 40 male rats. Blood samples for leuprolide and testosterone determinations were obtained from all groups pre-dose and at 4 and 24 h post-dose, and on Days 3, 5, 8, 15, 22, 29, 43, 57, 71, 85, 99, 113, 127, 141, 155, 169 and 183. Serum samples were analyzed for leuprolide and testosterone levels using a validated LC-MS/MS method with a lower limit of quantification (LLOQ) of 0.100 ng/mL for both, leuprolide and testosterone. The composite serum concentration-time data were used in the calculation of PK parameters of leuprolide using Phoenix® WinNonlin® 6.3.

Results

The mean Cmax values of leuprolide were reached at the first sample time, 4.0 h, following dosing in all leuprolide-treated groups.

Three- and 5-fold increases in dose from 6.8 mg to 20.3 mg and 33.8 mg resulted in 3.2- and 6.3-fold increases in Cmax values in male rats, respectively. The same 3- and 5-fold increases in dose resulted in 3.0 and 4.2-fold increases in AUC0-182 day in male rats, respectively, indicating that the dose proportionality of the Test Article was achieved with increasing doses in this study.

Ratios of dose normalized AUC0-182 day in the test article-treated groups (low dose, middle dose and high dose) to that in the reference article-treated group were 1.1, 1.1 and 0.9, respectively, indicating that dose-normalized drug exposure of leuprolide in all Test Article-treated groups during six months was comparable to that of the reference article group. Overall, all dose groups of the Test Article showed very similar exposure to that of the reference group, Eligard® 45 mg when normalized by dose.

PK results are summarized in the following table 7.

TABLE 7

PK Parameters of Leuprolide in Male Rats Following a Single Subcutaneous Administration of Four Different Treatments

| TK Parameters | Group 3 (Low dose) | Group 4 (Middle) | Group 5 (High dose) | Group 6 (Reference) |
|---|---|---|---|---|
| Dose level$^a$ (mg) | 6.8 | 20.3 | 33.8 | 30.0 |
| Leuprolide free base | 5.8 | 17.4 | 29.0 | 28.0 |
| $T_{max}$ (h) | 4.0 | 4.0 | 4.0 | 4.0 |
| $C_{max}$ (ng/mL) | 49.9 | 161 | 316 | 308 |
| $AUC_{0-182\ day}$ | 1047 | 3189 | 4383 | 4519 |
| $DNC_{max}$ | 8.60 | 9.25 | 10.9 | 11.0 |
| $DNAUC_{0-182\ day}$ | 181 | 183 | 151 | 161 |
| Ratio to low dose | | | | |
| $C_{max}$ | NC | 3.2 | 6.3 | NC |
| $AUC_{0-182\ day}$ | NC | 3.0 | 4.2 | NC |
| Ratio to reference | | | | |
| $DNC_{max}$ | 0.8 | 0.8 | 1.0 | NC |
| $DNAUC_{0-182\ day}$ | 1.1 | 1.1 | 0.9 | NC |

$^a$Based on leuprolide mesylate salt content.
$^b$ TK parameters were calculated based on the TK profile without abnormally high concentrations of leuprolide.
$DNC_{max}$: Dose normalized $C_{max}$ based on leuprolide free base.
$DNAUC_{0-182\ day}$: Dose normalized $DNAUC_{0-182\ day}$ based on leuprolide free base.
NC: Not calculated.

Following subcutaneous administration of all the Test Articles and reference article, the mean serum testosterone concentration decreased to below 0.500 ng/mL by Day 15~22, and maintained around such a level through the termination of the study in a similar fashion.

Conclusions

Male Sprague-Dawley rats were exposed to leuprolide via single subcutaneous injection of the Test Article at 6.8 mg, 20.3 mg and 33.8 mg or the reference article Eligard® 45 mg at 30 mg and monitored for 182 days. A relatively dose proportional increase in AUC was achieved for the middle and high doses of the Test Article when compared to the low dose. After dose normalization, all doses of the Test Article showed similar exposure of leuprolide to that of the reference article, Eligard® 45 mg.

Overall, LMIS 50 mg behaved similarly to the reference article, Eligard® 45 mg, both in drug exposure and suppression of serum testosterone in male rats for 6 months.

Example 5: The Effect of Leuprolide Salt Form on Formulation Delivery Duration

Two formulations were prepared using the same poly(D, L-lactide) (PLA) having a molecular weight of 16,000 Dalton. The PLA polymer used here was manufactured with a dodecanol (or lauryl alcohol) as an initiator resulting in the PLA polymer with one hydroxyl end group at one end and one dodecyl ester group at the other end. The PLA polymer was dissolved in NMP at a concentration of 60% by weight. Using this solution, formulations containing about 12% of leuprolide (by weight) were prepared. The leuprolide existed as mesylate salt having a molar ratio of methanesulfonic acid to leuprolide at 1.4:1 (LAMS1.4) in one formulation and as acetate salt having a molar ratio of methanesulfonic acid to leuprolide at 0:1 in another formulation (LAAc). The resulting formulations were then gamma irradiated at a dose of 25 kGy.

Figure 3:
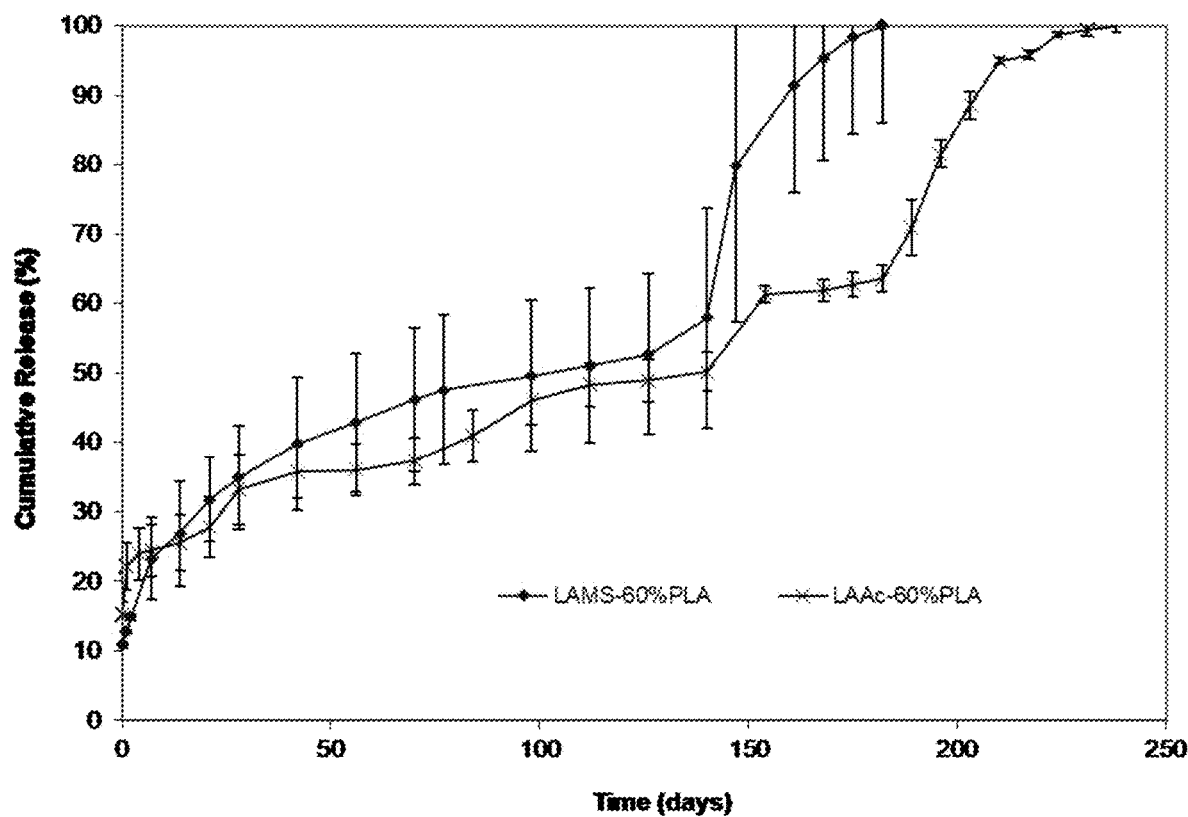
FIG. 3: In vitro release of LAMS and LAAc from PLA/NMP solution FIG. 4. LAMS release from Eligard® 45 mg polymer solution compared with Eligard® 45 mg release FIG. 5. In vitro release of leuprolide mesylate from different PLGA polymers compared with release from PLA polymer FIG. 6. In vitro release of LAMS from 8515PLGA polymers FIG. 7. Serum testosterone concentrations of male SD rats after injection of LAMS in PLGA/NMP formulations FIG. 8. In Vitro Release of Leuprolide from various PLA Formulations in PBS at pH 7.4 at 37° C.

The in vitro release of leuprolide was tested from these two formulations. The in vitro release test was performed in PBS at pH 7.4 at 37° C. and the release of leuprolide over time was measured by HPLC. Briefly, an aliquot of the formulation (about 100 mg) was injected into 3 mL phosphate buffer saline solution at pH 7.4 with 0.1% sodium azide at 37° C. The receiving fluid was replaced at pre-defined time points with fresh buffer solution, and the removed buffer solution diluted 2-fold with phosphate buffer at pH 7.4 was analyzed for drug concentration by HPLC. The amount released at each time point was calculated. FIG. 3 shows the cumulative release of leuprolide for different formulations over time.

As shown in FIG. 3 the release of leuprolide from the formulation with leuprolide mesylate completed (~180 days) faster than the formulation with leuprolide acetate (~240 days). This is not expected since the polymer molecular weight in the formulation is more stable with leuprolide mesylate than with leuprolide acetate under the same storage conditions. The in vitro release lasts more than 60 days longer when using leuprolide acetate versus using leuprolide mesylate in the formulation. The standard treatment duration for prostate cancer is 1, 3, 4 and 6 months. The enhanced formulation stability and 6-month delivery duration by using leuprolide mesylate instead of leuprolide acetate allow a better product, i.e., a single, ready-to-use prefilled syringe, to be developed to treat prostate cancer every 6-month.

Example 6: The Effect of the Salt Form of Leuprolide on Formulation Delivery Duration The in vitro release of leuprolide was tested from several kits of Eligard® 45 mg. These kits contain 1 syringe with leuprolide acetate (LAAc) and one syringe of polymer solution (PLGA8515 in NMP). PLGA8515 used here was prepared with hexanediol as an initiator and has a molar ratio of DL-lactide to Glycolide=85:15. The PLGA8515 polymer has one hydroxyl end group at both ends of the polymer chain. The two syringes are connected and the contents are mixed immediately prior to injection. The in vitro release test for Eligard® 45 mg was performed in phosphate buffered saline (PBS) at pH 7.4 at 37° C. and the release of leuprolide was measured by HPLC over time. Eligard® 45 mg was used to compare the release when leuprolide mesylate (LAMS1.4) was used in place of LAAc.

Figure 4:
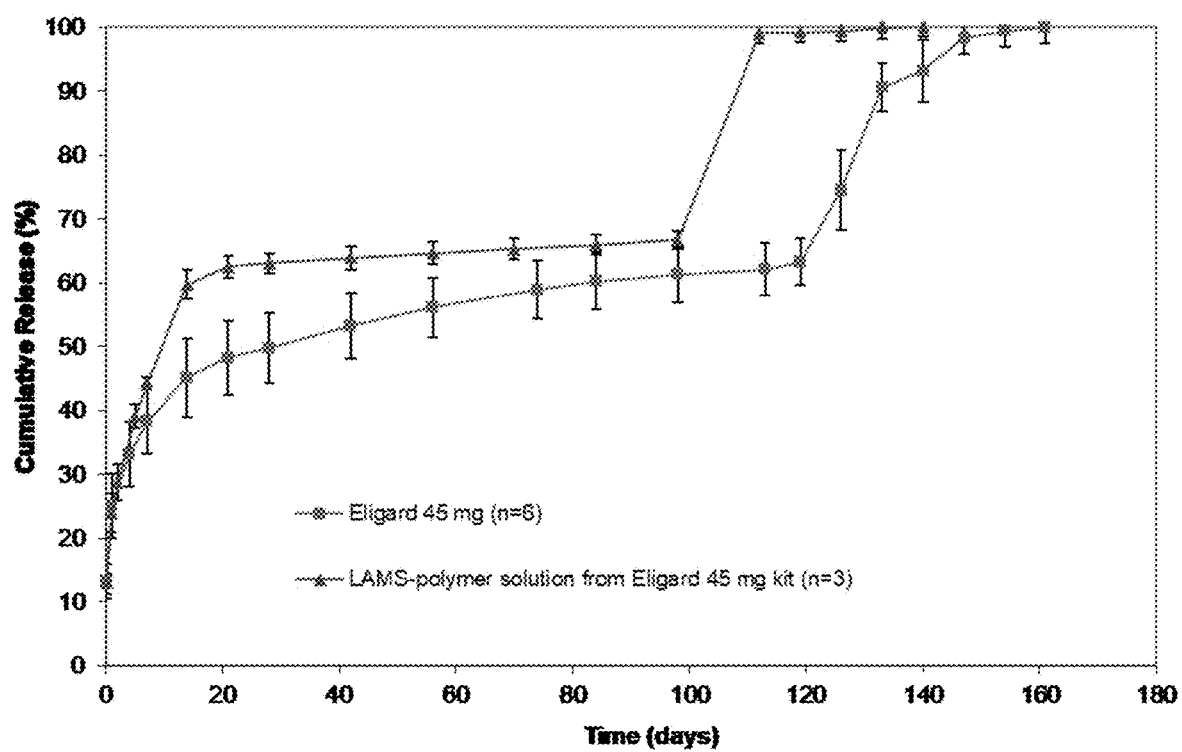

FIG. 4 shows the in vitro release of leuprolide from Eligard® 45 mg and compares with the release of leuprolide from a formulation using the polymer solution from an Eligard® 45 mg kit and leuprolide mesylate (LAMS) in place of LAAc. The release duration is much shorter when using LAMS in place of LAAc. The release with LAMS using the polymer syringe from the Eligard® kit was >99 released and the polymer was almost completely degraded at 112 days. The implants using the Eligard® 45 mg kit still remain after 160 days and are still releasing. This is quite surprising and counter intuitive since it has been previously found that the PLGA polymer is more stable in the formulation formulated with LAMS than that formulated with LAAc during storage.

Example 7: Delivery of Leuprolide Over 3 Months

Eligard® 22.5 mg can deliver leuprolide in order to suppress testosterone for 3 months. Eligard® 22.5 mg consists of 2 syringes, with leuprolide acetate in one syringe and the polymer solution in the other. The two are mixed immediately prior to injection. The polymer solution contains a 45% PLGA7525 polymer solution in NMP. The lower polylactide content results in a faster degradation than polymers with higher lactide content.

Figure 5:
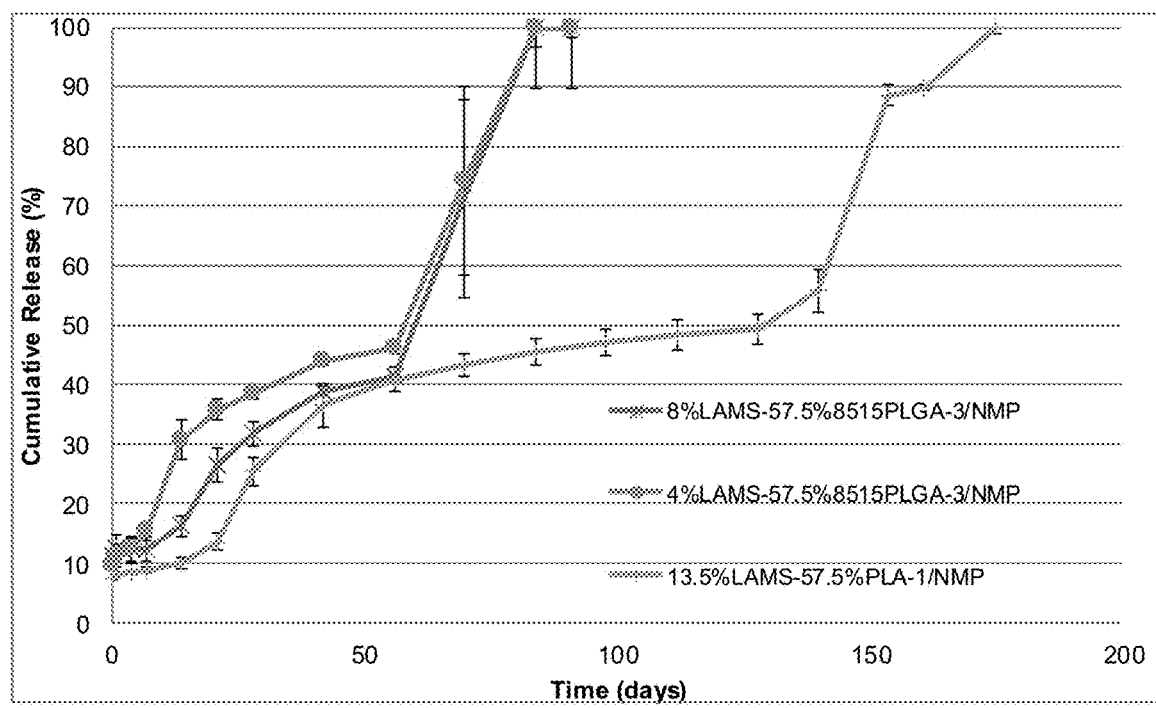

Formulations were made with leuprolide mesylate (LAMS(1.6)) in order to achieve the delivery of leuprolide for a period of 3 months. The leuprolide mesylate was prepared from leuprolide formate by salt exchange lyophilization process and contains a small amount of formic acid. These formulations are stable as a single syringe and can be directly injected. The release consisted of injection into 3 mL PBS buffer at 37° C. and pH 7.4. At each time point 2.5 mL of the releasing media was removed and replaced with fresh buffer. The removed release media was analyzed by HPLC for leuprolide content. FIG. 5 shows the release from several formulations tested in vitro.

The release of leuprolide is seen to be complete by about 3 months for the 8515PLGA formulations (PLGA-1: MW 12.6 k, PDI 1.8; PLGA-2: MW 15.5 k, PDI 1.5; PLGA-3 MW 20 k, PDI 2.5). The use of smaller molecular weight 8515PLGA can make the degradation duration even shorter than 3 months. The PLA polymer lasts for 6 months (PLA-1: MW 15 k, PDI 2.5). Eligard® 45 mg also uses a PLGA 8515 polymer, but the release lasts for 6 months. It was surprisingly found that using a PLGA8515 polymer with LAMS, the release can only last for 3 months. Therefore, an 8515PLGA polymer is needed when formulated with LAMS in order to maintain the delivery of leuprolide for a period of 3 months. Accordingly, by using LAMS and selecting PLGA having suitable MW and polydispersity, a formulation with a desired storage stability, release profile and duration can be prepared.

Example 8: Analysis of Implants Retrieved for Formulations Administered SC After 3 Months In Vivo in Rats Several formulations of leuprolide mesylate (LAMS1.6) with different 8515PLGA polymers were injected into male SD rats to test the duration of the release and compare with the release of LAMS from a formulation with PLA. After 91 days the implants were removed and analyzed to determine the remaining leuprolide content and the amount of polymer molecular weight degradation. Table 8 shows the data from the retrieved implants.

TABLE 8

Summary Analysis of Retrieved Implants

| Formulation | % MW Reduction | Leuprolide Remaining (% dose) |
|---|---|---|
| 8% LAMS-62.5% PLGA-1/NMP | 84.2 | 5.21 |
| 8% LAMS-60% PLGA-2/NMP | 85.7 | 0.67 |
| 8% LAMS-57.5% PLGA-3/NMP | 86.9 | 9.27 |
| 4% LAMS-57.5% PLGA-3/NMP | 84.9 | 12.19 |
| 13.5% LAMS-57.5% PLA-1/NMP | 45.5 | 48.61 |

The molecular weight for the 8515PLGA polymers has decreased by about 85% after 91 days, while the molecular weight of the PLA polymer has only been reduced by about 45%. The 8515PLGA polymers are almost completely done, which is also reflected by the amount of leuprolide remaining in the implants. About 5-10% of the initial leuprolide remains after 91 days. The PLA formulation still has about 50% left, which is about right if this formulation is for delivery for 6 months. Therefore, to deliver leuprolide for 3 months from a formulation with LAMS, an 8515PLGA polymer is needed, as opposed to the 7525PLGA polymer used in Eligard® 22.5 mg. This is surprising since the LAMS makes the formulation more stable than leuprolide acetate during storage. This unexpected property can be used to prepare more stable formulations for long term storage with suitable delivery durations.

Example 9: Effect of Leuprolide Content on Formulation Delivery Duration

Two formulations containing leuprolide mesylate (LAMS (1.65)) were prepared using a poly(D,L-lactide-co-glycolide) (PLGA) polymer. The PLGA polymer used here was manufactured with a dodecanol (or lauryl alcohol) as an initiator resulting in the PLGA copolymer with one hydroxyl end group at one end and one dodecyl ester group at the other end and has a molar ratio of DL-lactide to Glycolide=85:15. The PLGA polymer (MW 20 k, PDI 1.7) was dissolved in NMP at a concentration of 55% by weight. Using this solution, formulations containing 7.5% and 3.75% of leuprolide mesylate (LAMS1.65, by weight) were prepared. The resulting formulations were then irradiated using E-beam at a dose greater than 25 kGy.

The in vitro release of leuprolide was tested from these two formulations. The in vitro release test was performed in PBS at pH 7.4 at 37° C. and the release of leuprolide was measured by HPLC over time.

Figure 6:
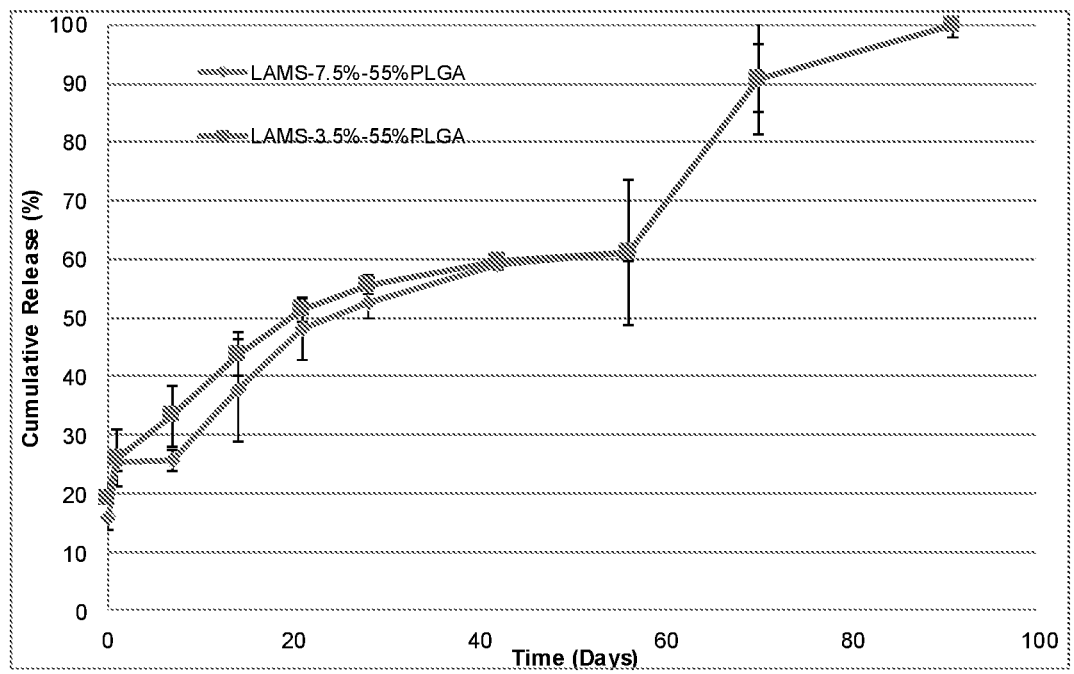

FIG. 6 shows the in vitro release of leuprolide from these two formulations. The release of leuprolide and the degradation of the PLGA polymer were completed in about 90 days. These formulations can be used to deliver leuprolide mesylate for a period of at least 3 months.

Figure 7:
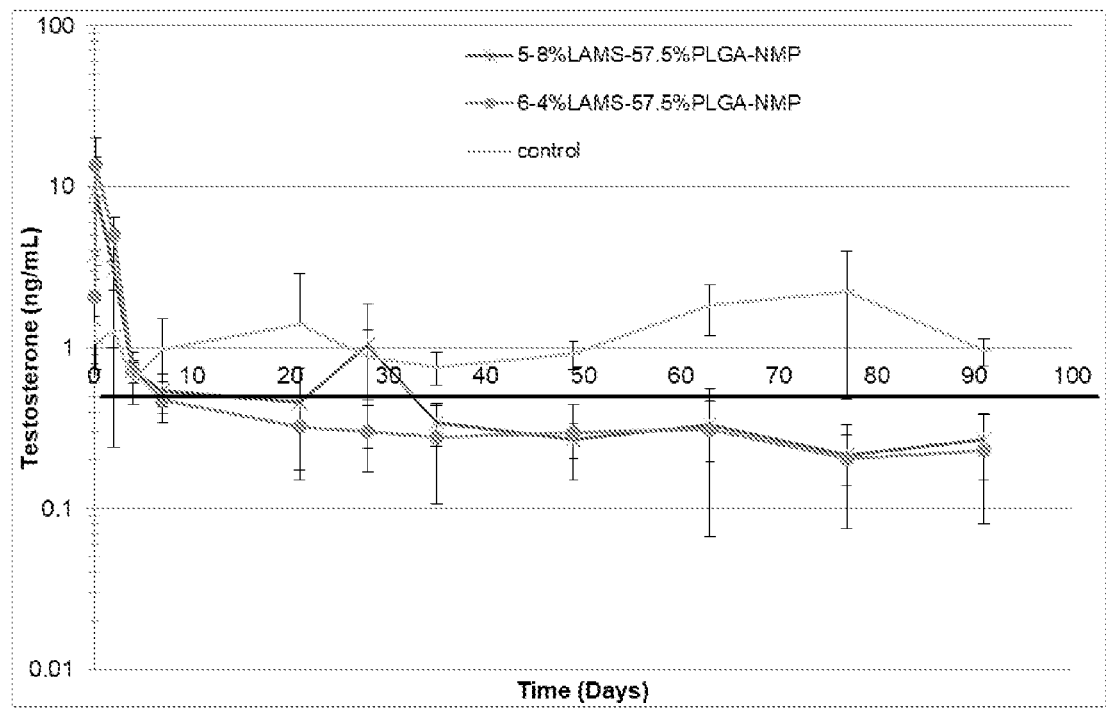

These two formulations were also evaluated by a single subcutaneous administration to male Sprague-Dawley rats to characterize the activity of leuprolide released from these formulations by the suppression of serum testosterone levels over time. Serum samples were analyzed for testosterone levels using a validated LC-MS/MS method with a lower limit of quantification (LLOQ) of 0.100 ng/mL. FIG. 7 shows the serum testosterone levels versus time. The serum testosterone levels in most of the rats were suppressed below human castrate level (≤0.5 ng/mL) 21 days post administration. For 7.5% LAMS in 55% PLGA/NMP solution, the average testosterone level went higher than 0.5 ng/mL at 28 days. This surge was due to the testosterone level in one rat, which was significantly higher than the rest. It's probably due to assay error or individual animal variability. Overall, the formulation prepared using PLGA polymer manufactured with a dodecanol (or lauryl alcohol) as an initiator, resulting in the PLGA copolymer with one hydroxyl end group at one end and one dodecyl ester group at the other end, and has a molar ratio of DL-lactide to Glycolide=85:15, can deliver a therapeutic level of leuprolide for a period of at least 3 months.

These results are quite unexpected. A similar formulation, the commercial product, Eligard® 45 mg, consisting of leuprolide acetate, PLGA having a molar ratio of DL-lactide to Glycolide=85:15, and NMP is approved for delivery of leuprolide for 6 months. It takes 6 months for the polymer used in Eligard® to degrade. The results confirm that leuprolide mesylate, in comparison with leuprolide acetate, can enhance the formulation stability, but can expedite the degradation of polymer during in vitro and in vivo release. These properties can be advantageously used to tailor and fine tune the formulation to prepare better product—a single, ready-to-use prefilled syringe. Such improved products are user friendly, eliminate the complicated mixing procedures, and avoid any dosing errors caused by the inappropriate mixing prior to administration.

Example 10: Formulations with Tailored Release Profiles or Delivery Durations Three formulations containing a mixture of leuprolide mesylate and leuprolide acetate were prepared using a poly(D,L-lactide-co-glycolide) (PLGA) polymer. The PLGA polymer used here was manufactured with a dodecanol (or lauryl alcohol) as an initiator resulting in the PLGA copolymer with one hydroxyl end group at one end and one dodecyl ester group at the other end and has a molar ratio of DL-lactide to Glycolide=85:15. The PLGA polymer was dissolved in NMP at a concentration of 55% by weight. Using this solution, formulations containing 7.5% of leuprolide (free base, by weight) were prepared. The ratios of leuprolide mesylate to leuprolide acetate are 1:0, 4:1, and 0:1 or the molar ratios of mesylate to leuprolide are 2:1, 1.6:1, and 0:1. The resulting formulations were then irradiated using E-beam at a dose greater than 25 kGy.

The in vitro release of leuprolide was tested from these two formulations. The in vitro release test was performed in PBS at pH 7.4 at 37° C. and the release of leuprolide was measured by HPLC over time.

The release of leuprolide and the degradation of the PLGA polymer were completed in about 90 days for formulation having the ratios of leuprolide mesylate to leuprolide acetate of about 1:0, in about 114 days for formulation having the ratio of about for 4:1, and in about 180 days for formulation having the ratio of 0:1. These formulations can be tailored to deliver leuprolide mesylate for a period from at least 3 months to 6 months by using a mixture of leuprolide salts formed with weak and strong acids.

Example 11: Formulations with Tailored Release Profiles or Delivery Durations Various release profile or delivery durations can be achieved by using different combinations of strong and weak acid salts of LHRH. Various salts of LHRH can be prepared according to the procedures known in the art. The mixture of salts may be prepared by mixing one weak acid LHRH salt with one strong acid salt to obtain desired ratios. Another way to prepare a mixture of LHRH salts it to add a strong acid to an aqueous solution of a weak acid LHRH salt. The strong acid ion can free or dissociate weak acid from the salt ion pair. The mixture can be freeze dried or lyophilized to remove liquid medium and any dissociated weak acid to obtain the desired mixture of the salts. The examples of weak acids include formic acid, acetic acid and strong acids include methanesulfonic acid, HCl, sulfuric acid, hydrogen bromide.

The mixture of leuprolide mesylate and leuprolide formate were prepared to have a ratio of leuprolide mesylate to leuprolide formate at 1:0, 9:1, 4:1, 7:3, and 0:1 or the ratios of mesylate to leuprolide are 2:1, 1.8:1, 1.6:1, 1.4:1, and 0:1. These salts can be formulated with PLGA in NMP solutions to obtain compositions with different delivery durations.

The leuprolide mesylate as disclosed herein can also be prepared by salt exchange by loading a leuprolide salt of a weak acid such as on an ion exchange column, washing off the weak acid from the column, eluting leuprolide off the column with a methane sulfonic acid solution to obtain leuprolide mesylate solution, and removing the liquid medium through evaporation and lyophilization to prepare the leuprolide mesylate dry powder.

Example 12: Formulations with LAMS of Mesylate to Leuprolide Ratios of 1.4-1.8

Figure 8:
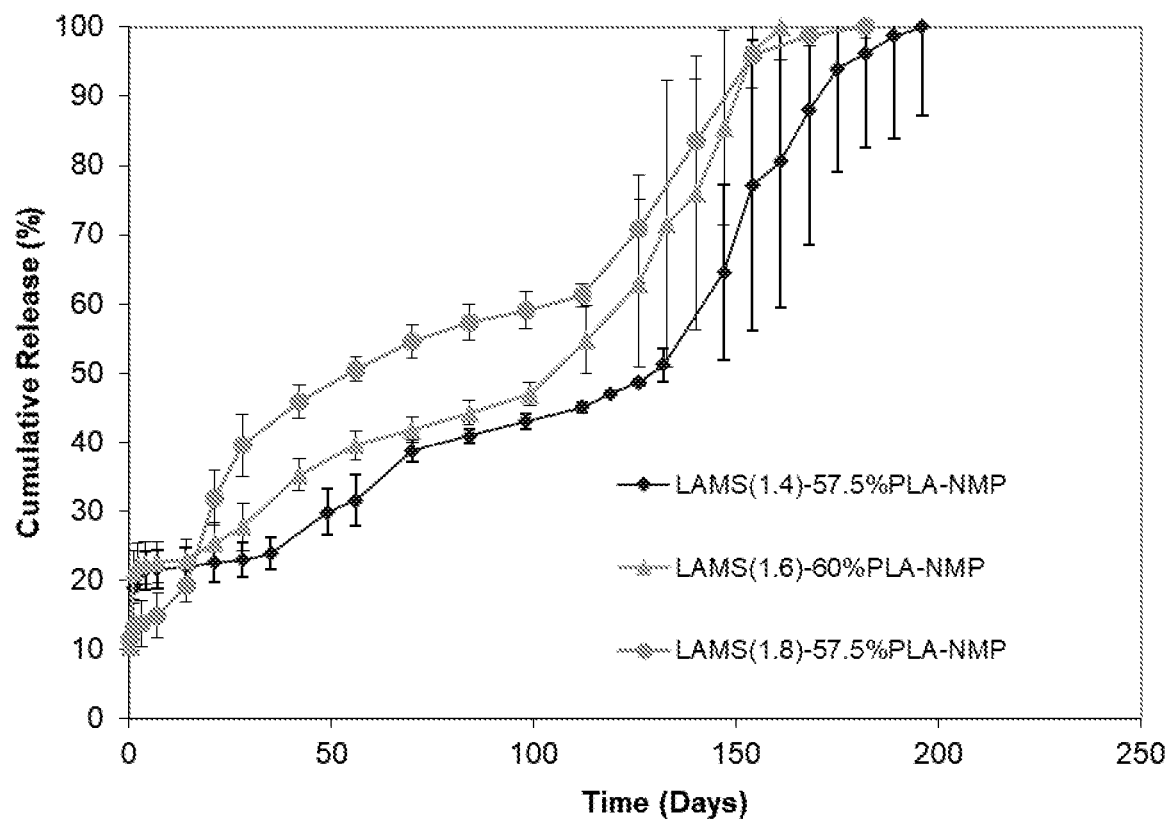

Formulations were prepared using a PLA polymer (MW 16 k PDI 1.8)) in NMP with leuprolide mesylate and were sterilized by gamma-irradiation at ~25 kGy. The in vitro release of these formulations were tested in phosphate buffer at pH 7.4 at 37° C. FIG. 8 shows that the in vitro release profiles of the formulations prepared using leuprolide mesylate with molar ratios of mesylate:leuprolide between 1.4 and 1.8. The leuprolide mesylate was prepared from leuprolide acetate by salt exchange and lyophilization process. The resulting leuprolide mesylate contains a small amount of acetate counter ion. The molar ratio of (mesylate+acetate) to leuprolide is ≤2:1. These formulations were prepared and tested for different periods of time. The polymer concentration was 57.5% in NMP. Overall, the in vitro release profiles of these formulations are comparable and all the formulations demonstrated a release duration of 6 months or slightly longer. The burst release of these formulations ranges from 10-25% with a duration of 6 months or slightly longer. These release profiles are similar to the in vitro release observed for the reference Eligard® 45 mg formulations.

Example 13: 1 Month Formulation Stability and Release

Formulations designed for a release duration of one month were made with a 50:50PLGA polymer (MW 50 k, PDI 4.0) in NMP using LAMS with a methane sulfonic acid to leuprolide ratio of 1.6:1 and 2.0:1. The formulations were stored at 25° C. and the peptide purity and polymer molecular weight were measured over time. Tables 9 and 10 show the peptide purity and molecular weight stability for these formulations respectively.

TABLE 9

Peptide purity at 25° C. in formulation with 25% PLGA50:50-NMP

| Time (wk) | LAMS(1.6) | LAMS(2.0) |
|---|---|---|
| 0 | 99.71 | 99.20 |
| 1 | 99.12 | 98.73 |
| 2 | 98.54 | 98.43 |
| 4 | 97.56 | 98.46 |
| 6 | 96.58 | 98.13 |
| 8 | 96.08 | 97.90 |

TABLE 10

Remaining polymer molecular weight as a percent of the original at 25° C. in formulation with 25% PLGA50:50-NMP

| Time (wk) | PLGA5050 | LAMS(1.6) | LAMS(2.0) |
|---|---|---|---|
| 0 | 100 | 100 | 100 |
| 1 | 93.6 | 87.7 | 92.2 |
| 2 | 95.1 | 91.3 | 95.6 |
| 4 | 95.5 | 86.9 | 94.1 |
| 6 | 94.6 | 84.0 | 94.8 |
| 8 | 88.3 | 68.8 | 87.6 |

Tables 9 and 10 show that the higher molar ratio of mesylate results in a more stable formulation with both peptide purity and polymer molecular weight showing better stability than the lower ratio. There is no difference in the polymer molecular weight degradation for the LAMS(2.0) compared to the polymer solution by itself. The release for these formulations is shown in FIG. 9. The release shows that the LAMS(2.0) has a higher initial release than the LAMS(1.6). Thus, the molar ratio of mesylate to leuprolide can be tuned to develop a formulation with desired storage stability and drug release duration.

What is claimed is:

1. A pharmaceutical composition comprising:
   a) a combination of a strong acid salt and a weak acid salt of a luteinizing hormone releasing hormone (LHRH) agonist wherein the molar ratio of (strong acid salt anion+weak acid salt anion) to the LHRH agonist is ≤2:1 and the molar ratio of the strong acid salt anion to the LHRH agonist is from 1:1 to less than 2:1;
   b) a biodegradable polymer selected from the group consisting of a homopolymer polylatic acid (PLA), and a copolymer poly (lactic acid-co-glycolic acid) (PLGA), wherein the ratio of lactic acid:glycolic acid of the copolymer is from 50:50 to 100:0; and
   c) N-methyl-2-pyrrolidone (NMP),
   wherein:
      the pharmaceutical composition has a selected release duration ranging from one month to 6 months, which correlates with ratios of the strong acid salt anion and the weak acid salt anion of the LHRH agonist;
      the LHRH agonist is selected from the group consisting of leuprolide, triptorelin, and goserelin; and
      the strong acid is methanesulfonic acid or hydrochloric acid, and the weak acid is acetic acid or formic acid.

2. The pharmaceutical composition of claim 1 wherein the LHRH agonist is leuprolide.

3. The pharmaceutical composition of claim 1 wherein the strong acid is methanesulfonic acid.

4. The pharmaceutical composition of claim 1 wherein the weak acid is formic acid.

5. The pharmaceutical composition of claim 1, wherein the strong acid salt is leuprolide mesylate, and the weak acid salt is leuprolide acetate.

6. The pharmaceutical composition of claim 5 wherein the molar ratio of mesylate anion to leuprolide is from 1.4:1 to less than 2:1.

7. The pharmaceutical composition of claim 5 wherein the molar ratio of mesylate anion to leuprolide is from 1.5:1 to 1.8:1.

8. A pharmaceutical composition comprising:
   a) a combination of leuprolide mesylate and leuprolide formate, wherein the molar ratio of (mesylate+formate) to leuprolide is ≤2:1 and the molar ratio of mesylate anion to leuprolide is from 1:1 to less than 2:1;
   b) a biodegradable polymer selected from the group consisting of a homopolymer polylatic acid (PLA), and a copolymer poly (lactic acid-co-glycolic acid) (PLGA), wherein the ratio of lactic acid:glycolic acid of the copolymer is from 50:50 to 100:0; and
   c) N-methyl-2-pyrrolidone (NMP);
      wherein the pharmaceutical composition has a selected release duration ranging from one month to 6 months, which correlate with ratios of mesylate to leuprolide.

9. The pharmaceutical composition of claim 8 wherein the molar ratio of mesylate anion to leuprolide is from 1.4:1 to less than 2:1.

10. The pharmaceutical composition of claim 8 wherein the molar ratio of mesylate anion to leuprolide is from 1.5:1 to 1.8:1.

11. The pharmaceutical composition of claim 1 wherein the biodegradable polymer has at least one hydroxyl terminal group.

12. The pharmaceutical composition of claim 5 wherein the biodegradable polymer has at least one hydroxyl terminal group.

13. The pharmaceutical composition of claim 8 wherein the biodegradable polymer has at least one hydroxyl terminal group.

14. The pharmaceutical composition of claim 1 wherein the pharmaceutical composition has 30 to 60% of the biodegradable polymer of the composition by weight, and a polydispersity less than or equal to 2.5.

15. The pharmaceutical composition of claim 14 wherein the biodegradable polymer has an average molecular weight of 8,000 to 50,000 Daltons.

* * * * *